(12) United States Patent
Mansoor et al.

(10) Patent No.: US 7,998,961 B2
(45) Date of Patent: Aug. 16, 2011

(54) HYDANTOIN DERIVATIVES USEFUL AS ANTIBACTERIAL AGENTS

(75) Inventors: Umar Faruk Mansoor, Framingham, MA (US); Panduranga Adulla P. Reddy, Walpole, MA (US); M. Arshad Siddiqui, Newton, MA (US)

(73) Assignee: Schering Corporation, Kenilworth, NJ (US)

( * ) Notice: Subject to any disclaimer, the term of this patent is extended or adjusted under 35 U.S.C. 154(b) by 190 days.

(21) Appl. No.: 11/846,804

(22) Filed: Aug. 29, 2007

(65) Prior Publication Data

US 2008/0226618 A1 Sep. 18, 2008

Related U.S. Application Data

(60) Provisional application No. 60/841,883, filed on Aug. 31, 2006.

(51) Int. Cl.
| | |
|---|---|
| *C07D 403/00* | (2006.01) |
| *C07D 405/00* | (2006.01) |
| *A61K 31/4965* | (2006.01) |
| *A01N 43/40* | (2006.01) |

(52) U.S. Cl. .................. 514/252.13; 514/326; 544/370; 546/210

(58) Field of Classification Search .......................... None
See application file for complete search history.

(56) References Cited

U.S. PATENT DOCUMENTS

| | | | |
|---|---|---|---|
| 5,925,659 | A | 7/1999 | Patchett et al. |
| 7,482,370 | B2 | 1/2009 | Yu et al. |
| 7,488,745 | B2 | 2/2009 | Yu et al. |
| 7,504,424 | B2 | 3/2009 | Yu et al. |
| 7,524,842 | B2 | 4/2009 | Lavey et al. |
| 7,687,527 | B2 | 3/2010 | Yu et al. |
| 2007/0265299 | A1 | 11/2007 | Lavey et al. |
| 2009/0111803 | A1 | 4/2009 | Yu et al. |
| 2009/0186874 | A1 | 7/2009 | Ikeura et al. |

FOREIGN PATENT DOCUMENTS

| | | |
|---|---|---|
| EP | 0572191 | 12/1993 |
| GB | 1321874 | 7/1973 |
| WO | WO98/33776 | 8/1998 |
| WO | WO2004/007444 | 1/2004 |
| WO | WO2004/020415 | 3/2004 |
| WO | WO2004/062601 | 7/2004 |
| WO | WO2008/027466 | 3/2008 |

OTHER PUBLICATIONS

Chawla et al., "Challenges in Polymorphism of Pharmaceuticals", CRIPS vol. 5, No. 1, Jan.-Mar. 2004 (4 Pages).*
Newman et al., "Solid-state analysis of the active pharmaceutical ingredient in drug products", DDT vol. 8, No. 19, Oct. 2003, p. 898-905.*
Ikeura et al, caplus an 2005:673263.*
International Search Report for International Application No. PCT/US2007/019063 dated Jan. 10, 2008.
T. Kline, et al.; "Potent, Novel, in Vitro Inhibitors of the *Pseudomonas aeruginosa* Deacetylase LpxC"; Journal of Medicinal Chemistry; 45:3112-3129 (2002).
Wensheng Yu et al., U.S. Appl. No. 12/338,425, filed Dec. 18, 2008 (Claims).
Wensheng Yu et al., U.S. Appl. No. 12/338,445, filed Dec. 18, 2008 (Claims).
Brian J. Lavey et al., U.S. Appl. No. 12/364,845, filed Feb. 3, 2009, (Claims).
Preliminary Amendment in U.S. Appl. No. 12/690,633, filed Jan. 20, 2010.
Notice of Allowance in U.S. Appl. No. 11/653,798 dated Oct. 6, 2009.
Notice of Allowance in U.S. Appl. No. 12/338,353 dated Oct. 15, 2009.
Notice of Allowance in U.S. Appl. No. 12/338,445 dated Oct. 30, 2009.

* cited by examiner

*Primary Examiner* — Sun Jae Loewe
(74) *Attorney, Agent, or Firm* — Eric A. Meade; Valerie J. Camara

(57) ABSTRACT

This invention relates to compounds of the Formula (I):

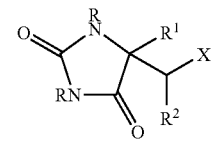

or a pharmaceutically acceptable salt, solvate, ester or isomer thereof, which is useful for the treatment of diseases or conditions mediated by LpxC.

3 Claims, No Drawings

HYDANTOIN DERIVATIVES USEFUL AS ANTIBACTERIAL AGENTS

CROSS-REFERENCE TO RELATED APPLICATIONS

This application claims the priority of Provisional Application No. 60/841,883, filed Aug. 31, 2006.

BACKGROUND OF THE INVENTION

1. Field of the Invention

This invention relates generally to hydantoin derivatives that can inhibit UDP-3-O—(R-3-hydroxymyristoyl)-N-acetylglucosamine deacetylase (LpxC), and as a result have antimicrobial activity.

2. Description

Lipid A is the hydrophobic anchor of lipopolysaccharide (LPS) and forms the major lipid component of the outer monolayer of the outer membrane of gram-negative bacteria. Lipid A is required for bacterial growth and inhibition of its biosynthesis is lethal to the bacteria. Furthermore, blocking Lipid A biosynthesis increases the sensitivity of bacteria to other antibiotics.

One of the key enzymes of bacterial lipid A biosynthesis is LpxC. LpxC catalyzes the removal of the N-acetyl group of UDP-3-O—(R-3-hydroxymyristoyl)-N-acetylglucosamine. The LpxC enzyme is essential in gram negative bacteria for the biosynthesis of Lipid A, and it is notably absent from mammalian genomes. Since LpxC is essential for Lipid A biosynthesis and inhibition of Lipid A biosynthesis is lethal to bacteria, inhibitors of LpxC have utility as antibiotics. In addition, the absence of LpxC from mammalian genomes reduces potential toxicity of LpxC inhibitors in mammals. Accordingly, LpxC is an attractive target for antibacterial drug discovery.

U.S. Pat. No. 5,925,659 teaches that certain heterocyclic hydroxamate compounds, in particular oxazoline compounds, have the ability to inhibit LpxC.

WO2004/00744 refers to N-Hydroxyamide derivatives having LpxC inhibitory activity and thus possessing antibacterial activity.

WO2004/062601 also refers to small molecule inhibitors of LpxC.

There is a need in the art for small molecule inhibitors of LpxC as potential antibacterial agents.

SUMMARY OF THE INVENTION

In its many embodiments, the present invention provides a novel class of compounds as inhibitors of LpxC, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with LpxC, using such compounds or pharmaceutical compositions.

In one embodiment, the present application discloses a compound, or pharmaceutically acceptable salts or solvates of said compound, said compound having the general structure shown in formula (I):

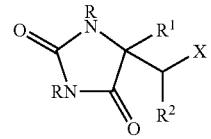

or a pharmaceutically acceptable salt, solvate, or ester thereof, wherein:

(i) X is selected from the group consisting of —C(O)NR$^3$R$^4$, —N(R$^5$)C(O)R$^6$, —N(R$^5$)C(O)NR$^3$R$^4$, —S(O)$_2$NR$^3$R$^4$, —N(R$^5$)S(O)$_2$R$^4$, —OR$^4$, —NR$^3$R$^4$, —SR$^4$, —S(O)R$^4$ and —S(O)$_2$R$^4$;

(ii) each R independently is selected from the group consisting of H, alkyl and cycloalkyl;

(iii) R$^1$ is selected from the group consisting of H, alkyl, cycloalkyl, heterocyclyl, aryl, heteroaryl, aralkyl, and heteroaralkyl,
   wherein each of said R$^1$ alkyl, cycloalkyl, heterocyclyl, aryl, heteroaryl, aralkyl, and heteroaralkyl is optionally independently substituted with 1-2 Y substituents;

(iv) R$^2$ is H or alkyl, wherein said alkyl is optionally, independently substituted with 1-2 Y substituents;

(v) R$^3$ is selected from the group consisting of H, alkyl, and cycloalkyl;

(vi) R$^4$ is selected from the group consisting of alkyl and aryl,
   wherein said R$^4$ alkyl is substituted with an aryl substituent, said aryl substituent of said R$^4$ alkyl being substituted with —C≡C-aryl,
   wherein said R$^4$ aryl is substituted with —C≡C-aryl, or (vii) wherein R$^3$ and R$^4$ together with the nitrogen atom to which they are shown attached are heterocyclyl or heteroaryl, wherein each of said heterocycyl or heteroaryl is substituted with at feast one aryl substituent,
   wherein said aryl substituent of said heterocyclyl or heteroaryl comprising R$^3$ and R$^4$ is substituted with one or two moieties selected independently from the group consisting of halogen, cyano, haloalkyl, alkoxy, haloalkoxy, alkyl, alkenyl, alkynyl, cycloalkyl, heterocyclyl, aryl, and heteroaryl,
      wherein the alkyl moiety of said aryl substituent is optionally substituted with a heteroaryl group,
      wherein the alkynyl moiety of said aryl substituent is optionally substituted with an aryl group;

(viii) R$^5$ is selected from the group consisting of H, alkyl, and cycloalkyl;

(ix) R$^6$ is aryl which is substituted with —C≡C-aryl;

(x) Y is selected from the group consisting of cyano, halogen, haloalkoxy, haloalkyl, —OR$^7$, —OC(O)R$^7$, —OC(O)NR$^8$R$^9$, —NR$^8$R$^9$, —N(R$^{10}$)C(O)R$^7$, —N(R$^{10}$)C(O)NR$^8$R$^9$—N(R$^{10}$)C(O)OR$^7$, —N(R$^{10}$)S(O)$_2$R$^7$, —SR$^7$, S(O)R$^7$, and S(O$_2$)R$^7$; and (xi) each R$^7$, R$^8$, R$^9$, and R$^{10}$ is independently selected from the group consisting of H, alkyl, cycloalkyl, heterocyclyl, aryl, heteroaryl, aralkyl, and heteroaralkyl.

The compounds of Formulae (I) are useful as inhibitors and may be useful in the treatment and prevention of diseases associated with LpxC.

DETAILED DESCRIPTION OF THE INVENTION

In its several embodiments, the present invention provides a novel class of inhibitors of LpxC, pharmaceutical compositions containing one or more of the compounds, methods of preparing pharmaceutical formulations comprising one or more such compounds and methods of treatment, prevention or amelioration of microbial infections.

In one embodiment, the present invention provides compounds which are represented by structural Formulae (I) above or a pharmaceutically acceptable salt, solvate, ester or isomer thereof, wherein the various moieties are as described above.

In another embodiment, in formula (I), X is —C(O)NR$^3$R$^4$.

In another embodiment, in formula (I), X is —C(O)NR$^3$R$^4$, wherein: R$^3$ is H or alkyl; and R$^4$ is selected from the group consisting of alkyl and aryl, wherein said R$^4$ alkyl is substituted with an aryl substituent, said aryl substituent of said R$^4$ alkyl being substituted with CC-aryl, and wherein said R$^4$ aryl is substituted with —C≡C-aryl.

In another embodiment, in formula (I), each R is H; and R$^1$ is alkyl which is optionally substituted with 1-2 Y substituents.

In another embodiment, in formula (I), each R is H; R$^1$ is alkyl which is optionally substituted with 1-2 Y substituents; X is —C(O)NR$^3$R$^4$, wherein: R$^3$ is H or alkyl; and R$^4$ is selected from the group consisting of alkyl and aryl, wherein said R$^4$ alkyl is substituted with an aryl substituent, said aryl substituent of said R$^4$ alkyl being substituted with —C≡C-aryl, and wherein said R$^4$ aryl is substituted with —C≡C-aryl.

In another embodiment, in formula (I), the R$^1$ alkyl is methyl.

In another embodiment, in formula (I), R$^2$ is H.

In another embodiment, in formula (I), R$^3$ is H.

In another embodiment, in formula (I), R$^4$ is alkyl, wherein said R$^4$ alkyl is substituted with an aryl substituent, wherein said aryl substituent of said R$^4$ alkyl is substituted with —C≡C-aryl.

In another embodiment, in formula (I), R$^4$ is alkyl, wherein said R$^4$ alkyl is selected from the group consisting of —CH$_2$CH$_2$— and —CH(CH$_3$)—; wherein said R$^4$ alkyl is substituted with an aryl substituent, wherein said aryl substituent of said R$^4$ alkyl is substituted with —C≡C-aryl.

In another embodiment, in formula (I), R$^4$ is alkyl, wherein said R$^4$ alkyl is substituted with an aryl substituent, wherein said aryl is phenyl, wherein said phenyl substituent of said R$^4$ alkyl is substituted with —C≡C-aryl.

In another embodiment, in formula (I), R$^4$ is alkyl wherein said R$^4$ alkyl is substituted with an aryl substituent, wherein said aryl is phenyl, wherein said phenyl substituent of said R$^4$ alkyl is substituted with —C≡C-aryl, wherein said aryl of said —C≡C-aryl is phenyl.

In another embodiment, in formula (I), R$^4$ is aryl, wherein said R$^4$ aryl is substituted with —C≡C-aryl.

In another embodiment, in formula (I), R$^4$ is aryl, wherein said R$^4$ aryl is substituted with —C≡C-aryl, wherein said R$^4$ aryl is phenyl.

In another embodiment, in formula (I), R$^4$ is aryl, wherein said R$^4$ aryl is substituted with —C≡C-aryl; wherein the aryl of said —C≡C-aryl is phenyl.

In another embodiment, in formula (I), X is —C(O)NR$^3$R$^4$; R$^3$ and R$^4$ together with the nitrogen atom to which they are shown attached are heterocyclyl or heteroaryl, wherein each of said heterocycyl or heteroaryl is substituted with at least one aryl substituent; wherein said aryl substituent of said heterocyclyl or heteroaryl comprising R$^3$ and R$^4$ is substituted with one or two moieties selected independently from the group consisting of halogen, cyano, haloalkyl, alkoxy, haloalkoxy, alkyl, alkenyl, alkynyl, cycloalkyl, heterocyclyl, aryl, and heteroaryl; wherein the alkyl moiety of said aryl substituent is optionally substituted with a heteroaryl group; wherein the alkynyl moiety of said aryl substituent is optionally substituted with an aryl group.

In another embodiment, in formula (I), each R is H; X is —C(O)NR$^3$R$^4$; R$^3$ and R$^4$ together with the nitrogen atom to which they are shown attached are heterocyclyl or heteroaryl, wherein each of said heterocycyl or heteroaryl is substituted with at least one aryl substituent; wherein said aryl substituent of said heterocyclyl or heteroaryl comprising R$^3$ and R$^4$ is substituted with one or two moieties selected independently from the group consisting of halogen, cyano, haloalkyl, alkoxy, haloalkoxy, alkyl, alkenyl, alkynyl, cycloalkyl, heterocyclyl, aryl, and heteroaryl; wherein the alkyl moiety of said aryl substituent is optionally substituted with a heteroaryl group: wherein the alkynyl moiety of said aryl substituent is optionally substituted with an aryl group.

In another embodiment, in formula (I), each R is H; X is —C(O)NR$^3$R$^4$; R$^3$ and R$^4$ together with the nitrogen atom to which they are shown attached are heterocyclyl; wherein said heterocycyl comprising R$^3$ and R$^4$ is substituted with at least one aryl substituent; wherein said aryl substituent of said heterocyclyl comprising R$^3$ and R$^4$ is substituted with one or two moieties selected independently from the group consisting of halogen, alkyl, alkynyl, cycloalkyl, heterocyclyl, aryl, and heteroaryl; wherein the alkyl moiety of said aryl substituent is optionally substituted with a heteroaryl group; wherein the alkynyl moiety of said aryl substituent is optionally substituted with an aryl group.

In another embodiment, in formula (I), each R is H; X is —C(O)NR$^3$R$^4$; R$^3$ and R$^4$ together with the nitrogen atom to which they are shown attached are heterocyclyl; wherein said heterocycyl comprising R$^3$ and R$^4$ is substituted with at least one aryl substituent; wherein said aryl substituent of said heterocyclyl comprising R$^3$ and R$^4$ is substituted with one or two moieties selected independently from the group consisting of halogen, alkyl, alkynyl, cycloalkyl, heterocyclyl, aryl, and heteroaryl; wherein the alkyl moiety of said aryl substituent is optionally substituted with a heteroaryl group; wherein the alkynyl moiety of said aryl substituent is optionally substituted with an aryl group; wherein said heterocyclyl comprising R$^3$ and R$^4$ is selected from the group consisting of piperidine and piperazine.

In another embodiment, in formula (I), each R is H; X is —C(O)NR$^3$R$^4$; R$^3$ and R$^4$ together with the nitrogen atom to which they are shown attached are heterocyclyl; wherein said heterocycyl comprising R$^3$ and R$^4$ is substituted with at least one aryl substituent; wherein said aryl substituent of said heterocyclyl comprising R$^3$ and R$^4$ is substituted with one or two moieties selected independently from the group consisting of halogen, alkyl, alkynyl, cycloalkyl, heterocyclyl, aryl, and heteroaryl; wherein the alkyl moiety of said aryl substituent is optionally substituted with a heteroaryl group; wherein the alkynyl moiety of said aryl substituent is optionally substituted with an aryl group; wherein said aryl substituent of said heterocyclyl comprising R$^3$ and R$^4$ is phenyl.

In another embodiment, in formula (I), each R is H; X is —C(O)NR$^3$R$^4$; R$^3$ and R$^4$ together with the nitrogen atom to which they are shown attached are heterocyclyl; wherein said heterocycyl comprising R$^3$ and R$^4$ is substituted with at least one aryl substituent; wherein said aryl substituent of said heterocyclyl comprising R$^3$ and R$^4$ is substituted with one or two moieties selected independently from the group consisting of halogen, alkyl, alkynyl, cycloalkyl, heterocyclyl, aryl, and heteroaryl; wherein the alkyl moiety of said aryl substituent is optionally substituted with a heteroaryl group; wherein the alkynyl moiety of said aryl substituent is optionally substituted with an aryl group; wherein said aryl group of said alkynyl moiety is phenyl.

In another embodiment, in formula (I), each R is H; X is —C(O)NR³R⁴; R³ and R⁴ together with the nitrogen atom to which they are shown attached are heterocyclyl; wherein said heterocycyl comprising R³ and R⁴ is substituted with two substituents, one of which is optionally substituted aryl, and the other is hydroxyl; wherein the aryl substituent of said heterocyclyl comprising R³ and R⁴ is optionally substituted with one or two moieties selected independently from the group consisting of halogen, alkyl, alkynyl, cycloalkyl, heterocyclyl, aryl, and heteroaryl; wherein the alkyl moiety of said aryl substituent is optionally substituted with a heteroaryl group; wherein the alkynyl moiety of said aryl substituent is optionally substituted with an aryl group.

In another embodiment, in formula (I), each R is H; X is —C(O)NR³R⁴; R¹ is alkyl selected from the group consisting of methyl and ethyl, each of which is optionally substituted with 1-2 substitutents independently selected from the group consisting of hydroxyl or —NH₂; R³ and R⁴ together with the nitrogen atom to which they are shown attached are heterocyclyl; wherein the aryl substituent of said heterocyclyl comprising R³ and R⁴ is optionally substituted with one or two moieties selected independently from the group consisting of halogen, alkyl, alkynyl, cycloalkyl, heterocyclyl, aryl, and heteroaryl; wherein the alkyl moiety of said aryl substituent is optionally substituted with a heteroaryl group; wherein the alkynyl moiety of said aryl substituent is optionally substituted with an aryl group.

In another embodiment, in formula (I), each R is H; X is —C(O)NR³R⁴; R¹ is heterocyclyl selected from the group consisting of piperidine and pyrrolidine, each of which is optionally substituted with a hydroxyl; R³ and R⁴ together with the nitrogen atom to which they are shown attached are heterocyclyl; wherein the aryl substituent of said heterocyclyl comprising R³ and R⁴ is optionally substituted with one or two moieties selected independently from the group consisting of halogen, alkyl, alkynyl, cycloalkyl, heterocyclyl, aryl, and heteroaryl; wherein the alkyl moiety of said aryl substituent is optionally substituted with a heteroaryl group; wherein the alkynyl moiety of said aryl substituent is optionally substituted with an aryl group.

In another embodiment, in formula (I), each R is H; X is —C(O)NR³R⁴; R¹ is cycloalkyl selected from the group consisting of cyclopentyl and cyclohexyl, each of which is optionally substituted with a hydroxyl; R³ and R⁴ together with the nitrogen atom to which they are shown attached are heterocyclyl; wherein the aryl substituent of said heterocyclyl comprising R³ and R⁴ is optionally substituted with one or two moieties selected independently from the group consisting of halogen, alkyl, alkynyl, cycloalkyl, heterocyclyl, aryl, and heteroaryl; wherein the alkyl moiety of said aryl substituent is optionally substituted with a heteroaryl group; wherein the alkynyl moiety of said aryl substituent is optionally substituted with an aryl group.

In another embodiment, in formula (I), X is —N(R⁵)C(O)R⁶, wherein R⁵ is H or alkyl; and R⁶ is aryl which is substituted with a —C≡C-aryl.

In another embodiment, in formula (I), wherein each R is H; X is —N(R⁵)C(O)R⁶, wherein R⁵ is H or alkyl; and R⁶ is aryl which is substituted with a —C≡C-aryl.

In another embodiment, in formula (I), R¹ is H; X is —N(R⁵)C(O)R⁶, wherein R⁵ is H or alkyl; and R⁶ is aryl which is substituted with a —C≡C-aryl.

In another embodiment, in formula (I), R² is alkyl which is optionally substituted with a hydroxy substituent; X is —N(R⁵)C(O)R⁶, wherein R⁵ is H or alkyl; and R⁶ is aryl which is substituted with a —C≡C-aryl.

In another embodiment, in formula (I), X is —N(R⁵)C(O)R⁶ wherein R⁵ is H; and R⁶ is phenyl which is substituted with a —C≡C-aryl.

In another embodiment, in formula (I), X is —N(R⁵)C(O)R⁶, wherein R⁵ is H; and R⁶ is phenyl which is substituted with a —C≡C-aryl; wherein said aryl of —C≡C-aryl is phenyl.

In another embodiment, in formula (I), X is —N(R⁵)C(O)NR³R⁴.

In another embodiment, in formula (I), X is —N(R⁵)C(O)NR³R⁴; wherein: R³ and R⁴ together with the nitrogen atom to which they are shown attached are heterocyclyl or heteroaryl, wherein each of said heterocycyl or heteroaryl is substituted with at least one aryl substituent; and R⁵ is H or alkyl.

In another embodiment, in formula (I), X is —N(R⁵)C(O)NR³R⁴; wherein: R³ and R⁴ together with the nitrogen atom to which they are shown attached are heterocyclyl, wherein said heterocycyl is substituted with one aryl substituent, wherein said aryl substituent is substituted with an alkynyl moiety, wherein said alkynyl moiety is substituted with an aryl group; and R⁵ is H or alkyl.

In another embodiment, in formula (I), X is —N(R⁵)C(O)NR³R⁴; wherein: R³ and R⁴ together with the nitrogen atom to which they are shown attached are heterocyclyl, wherein said heterocycyl is piperidinyl which is substituted with one aryl substituent, wherein said aryl substituent is substituted with an alkynyl moiety, wherein said alkynyl moiety is substituted with an aryl group; and R⁵ is H or alkyl.

In another embodiment, in formula (I), X is —N(R⁵)C(O)NR³R⁴; wherein: R³ and R⁴ together with the nitrogen atom to which they are shown attached are heterocyclyl, wherein said heterocycyl is piperidinyl which is substituted with one aryl substituent, which is phenyl substituted with an alkynyl moiety, wherein said alkynyl moiety is substituted with an aryl group which is phenyl; and R⁵ is H or alkyl.

In another embodiment, in formula (I), X is —N(R⁵)C(O)NR³R⁴; wherein: R³ and R⁴ together with the nitrogen atom to which they are shown attached are heterocyclyl or heteroaryl, wherein each of said heterocycyl or heteroaryl is substituted with at least one aryl substituent; and R⁵ is H.

In another embodiment, in formula (I), X is —N(R⁵)S(O)₂R⁴.

In another embodiment, in formula (I), X is —N(R⁵)S(O)₂R⁴ wherein R⁵ is H.

In another embodiment, in formula (I), X is —N(R⁵)S(O)₂R⁴ wherein R⁵ is H; and R⁴ is aryl substituted with a —C≡C-aryl.

In another embodiment, in formula (I), X is N(R⁵)S(O)₂R⁴, wherein R⁵ is H; and R⁴ is aryl substituted with a —C≡C-aryl; wherein said R⁴ aryl is phenyl.

In another embodiment, in formula (I), X is —N(R⁵)S(O)₂R⁴, wherein R⁵ is H; and R⁴ is aryl substituted with a —C≡C-aryl; wherein said R⁴ aryl is phenyl; and wherein the aryl of —C≡C-aryl is phenyl.

In another embodiment, in formula (I), X is —OR⁴.

In another embodiment, in formula (I), X is —OR⁴, wherein R⁴ is aryl which is substituted with a —C≡C-aryl.

In another embodiment, in formula (I), X is —NR³R⁴.

In another embodiment, in formula (I), X is NR³R⁴, wherein R³ is H, and R⁴ is aryl which is substituted with a —C≡C-aryl.

In another embodiment, in formula (II), X is —SR⁴.

In another embodiment, in formula (I), X is —SR⁴, wherein R⁴ is aryl which is substituted with a C≡C-aryl.

In another embodiment, in formula (I) X is —S(O)R⁴.

In another embodiment, in formula (I), X is —S(O)R⁴, wherein R⁴ is aryl which is substituted with a —C≡C-aryl.

In another embodiment, in formula (I), X is —S(O)R[4].
In another embodiment, in formula (I), X is —S(O)₂R[4], wherein R[4] is aryl which is substituted with a —C≡C-aryl.
In another embodiment, the compounds of formula (I) are selected from the group consisting of:
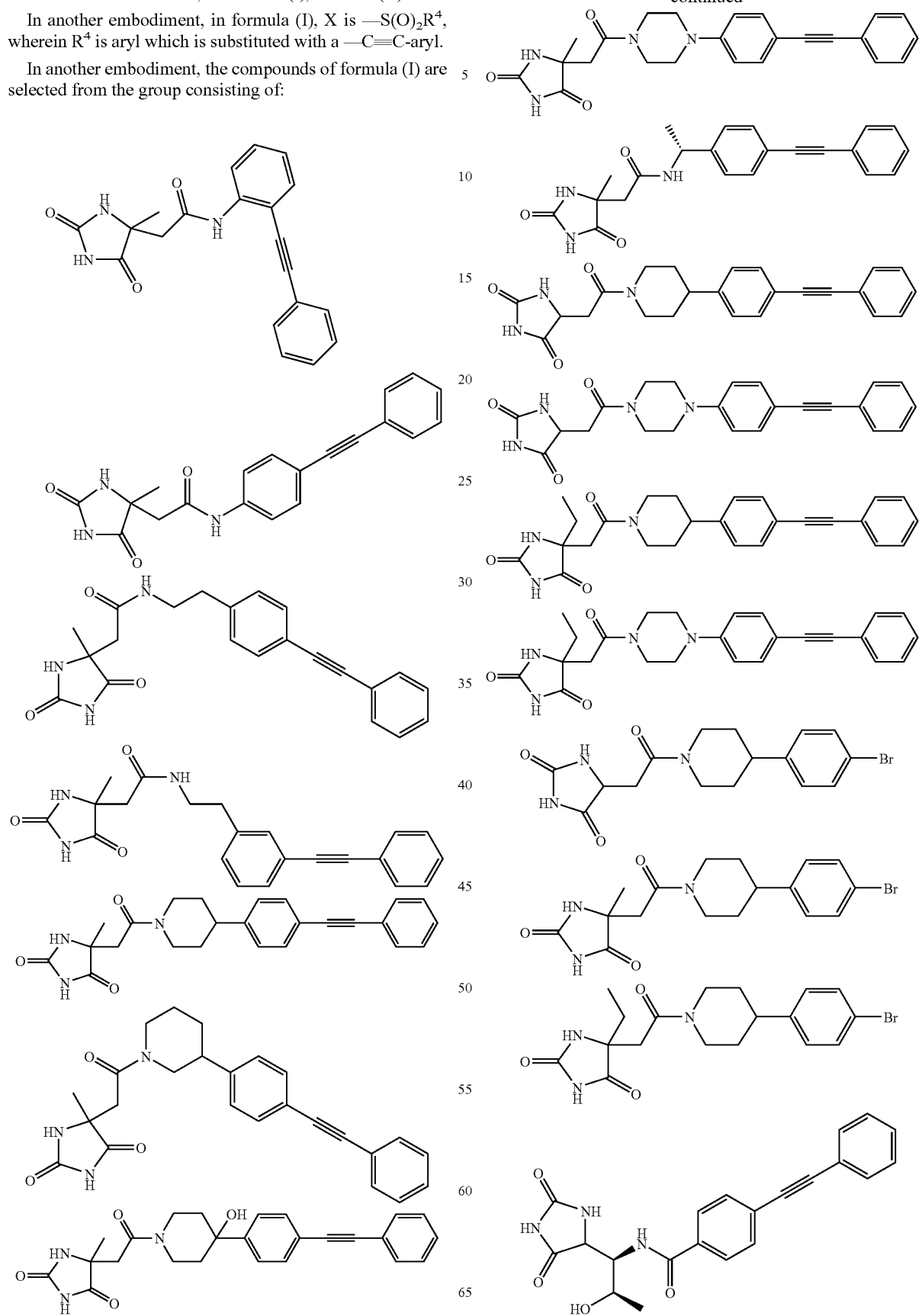

-continued
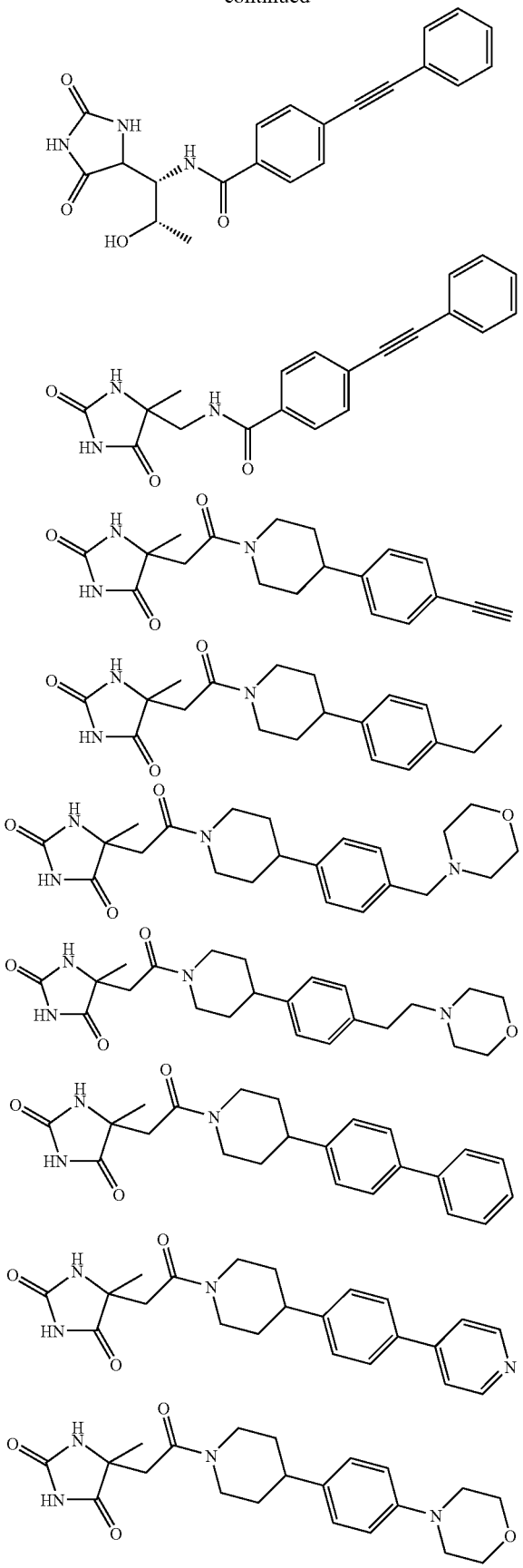
-continued
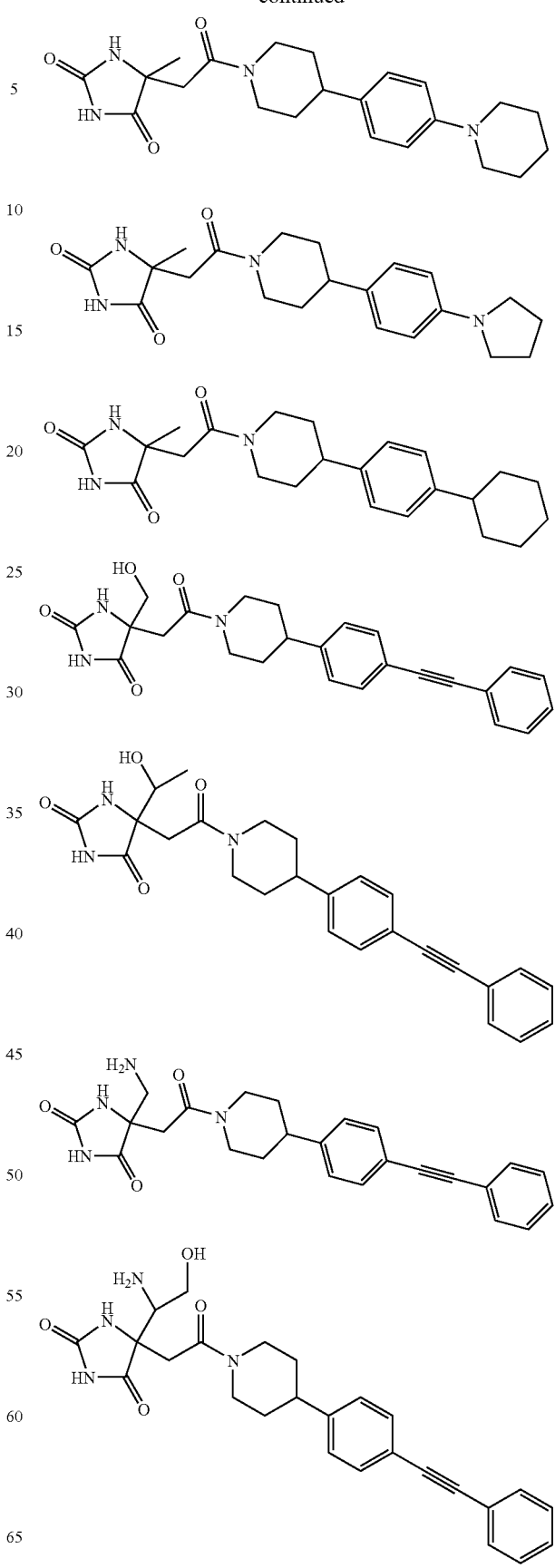

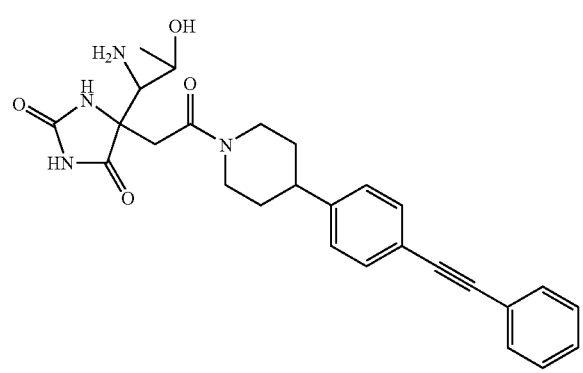
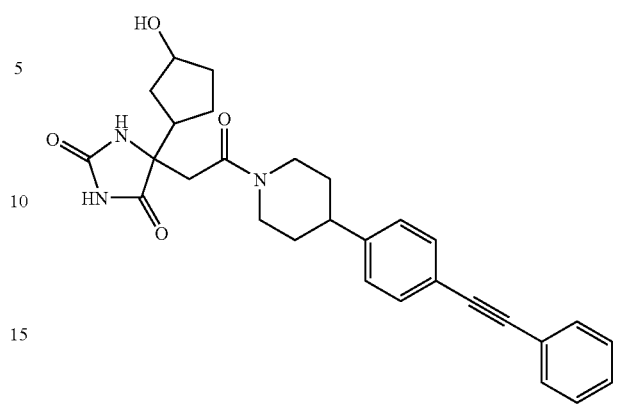
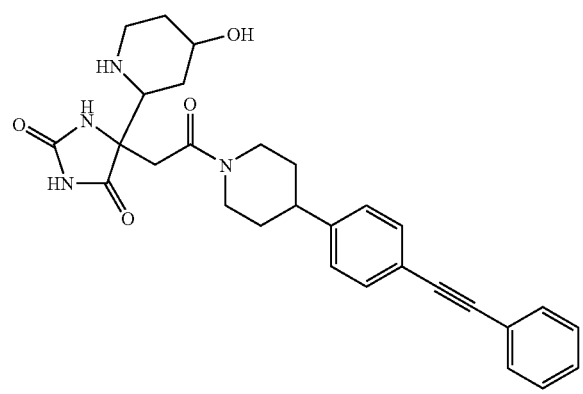
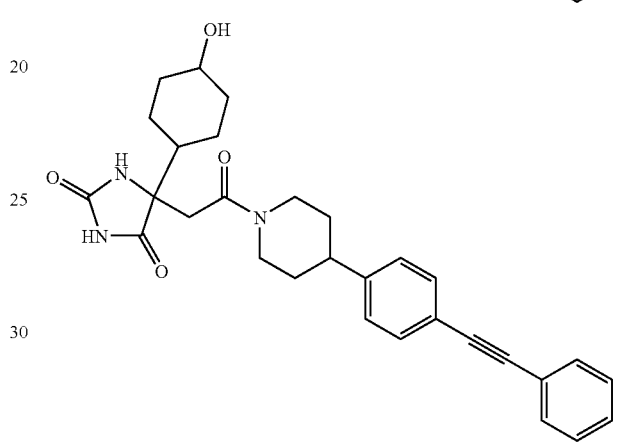
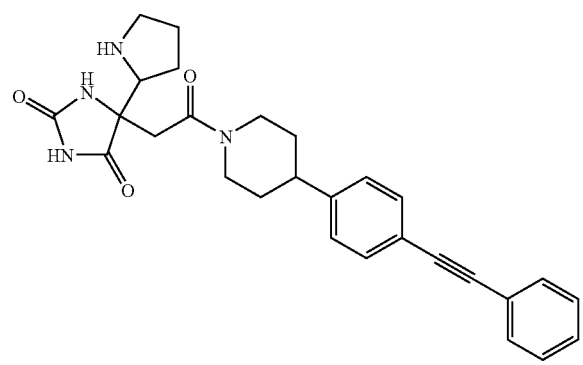
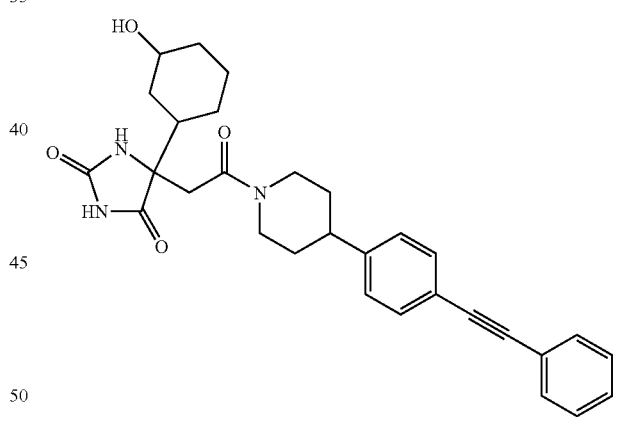
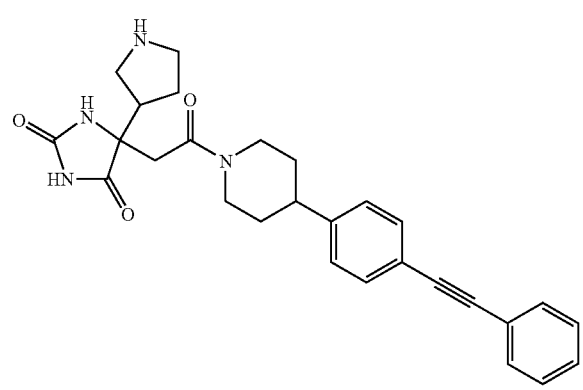
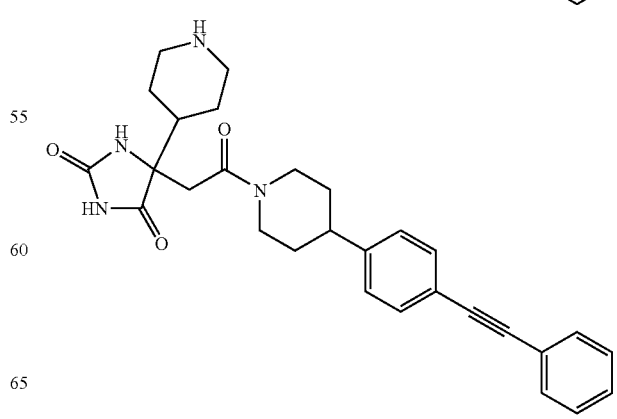

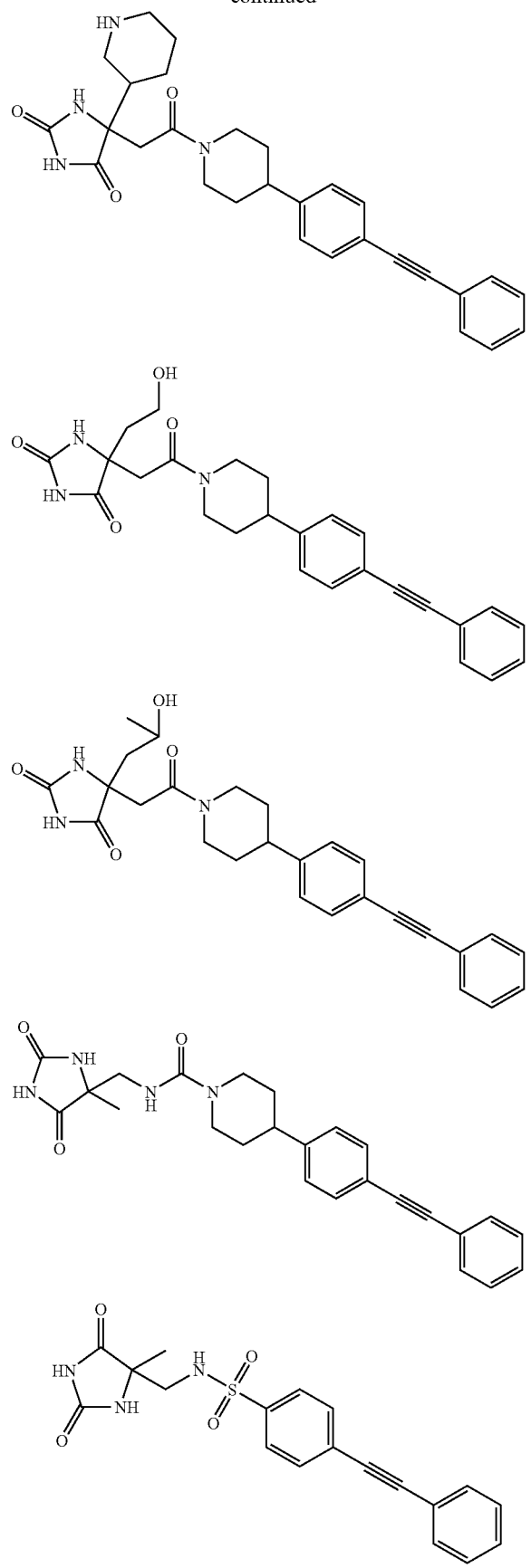
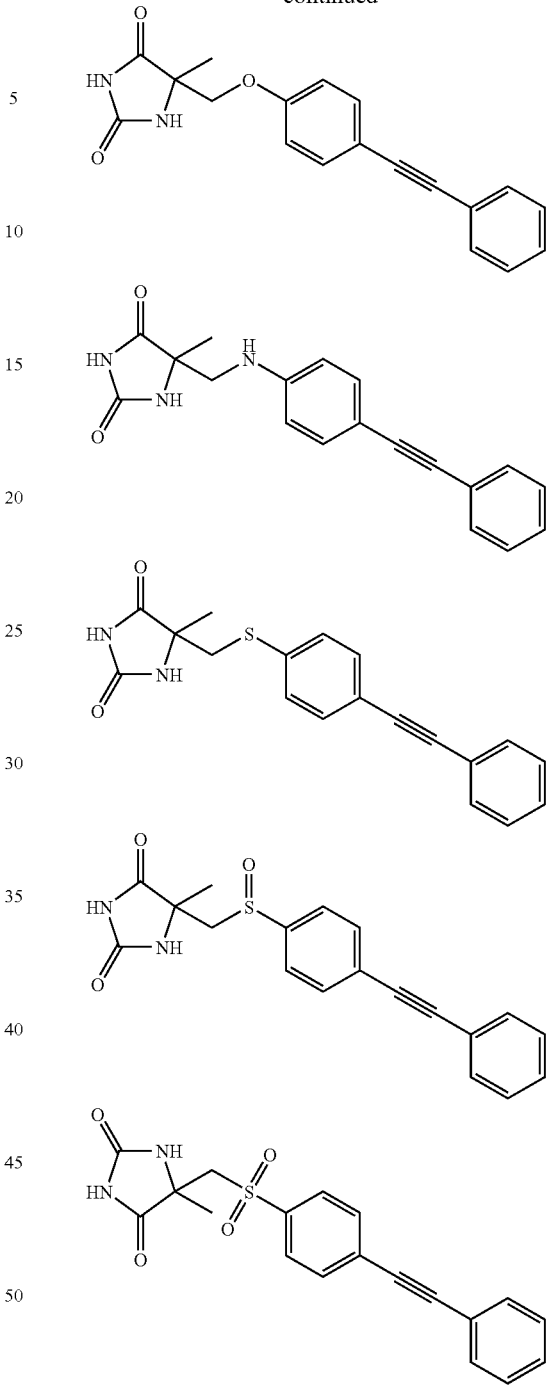

or a pharmaceutically acceptable salt, solvate or ester thereof.

As used above, and throughout this disclosure, the following terms, unless otherwise indicated, shall be understood to have the following meanings:

"Patient/subject" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and C(O)O-alkyl, Non-limiting examples of suitable alkyl groups include methyl, ethyl, n-propyl, isopropyl and t-butyl. The term "Fluoroalkyl" means an alkyl group in which alkyl is as previously described wherein one or more hydrogens are replaced with fluorine atoms.

"Alkenyl" means an aliphatic hydrocarbon group containing at (east one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain, Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein, Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkenyl" means a non-aromatic mono or multicyclic ring system comprising about 3 to about 10 carbon atoms, preferably about 5 to about 10 carbon atoms which contains at leas, one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Haloalkyl" means an alkyl as defined above wherein one or more hydrogen atoms on the alkyl is replaced by a halo group defined above, Non-limiting examples include trifluoromethyl, 2,2,2-trifluoroethyl, 2-chloropropyl and alike.

"Haloalkoxy" means an alkoxy group as defined below wherein one or more hydrogen atoms on the alkoxy is replaced by a halo/halogen group defined above. Non-limiting examples include trifluoromethoxy ($CF_3O$—), difluoromethoxy ($CHF_2O$—), 2,2,2-trifluoroethoxy ($CF_3CH_2O$—), 2-chloropropoxy ($CH_3CH(Cl)CH_2O$—) and alike.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

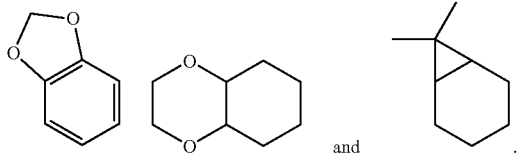

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

"Heterocyclenyl" means a partially unsaturated monocyclic or partially unsaturated multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heterocyclenyls contain about 5 to about 6 ring atoms and 1-3 double bonds. Preferred heterocyclenyls also contain at least one —C=N as part of the ring. The "heterocyclenyl" can be optionally substituted by one or more "ring system substituents" which may be the same or different, and are as defined herein. The prefix aza, oxa or thia before the heterocyclenyl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heterocyclenyls include dihydroimidizole, dihydrooxazole, dihydroxadiazole, dihydrothiazole, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

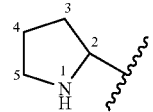

there is no —OH attached directly to carbons marked 2 and 5.

It should also be noted that tautomeric forms such as, for example, the moieties:

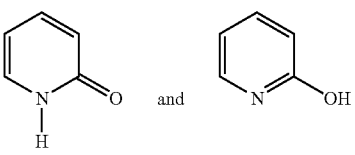

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described, Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl, "Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl, "Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al. *Protective Groups in organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto, "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic ameliorative, inhibitory or preventative effects.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1-19; P. Gould, *International J. of Pharmaceutics* (1986) 33 201-217; Anderson et al, *The Practice of Medicinal Chemistry* (1996). Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates and prodrugs of the compounds of Formula I, are intended to be included in the present invention.

The compounds according to the invention have pharmacological properties; in particular, the compounds of Formula I are inhibitors of LpxC.

In one aspect, the invention provides a pharmaceutical composition comprising as an active ingredient at least one compound of formula (I).

In another aspect, the invention provides a pharmaceutical composition of formula (I) additionally comprising at least one pharmaceutically acceptable carrier.

In another aspect, the invention provides a method of treating disorders associated with LpxC, said method comprising administering to a patient in need of such treatment a pharmaceutical composition which comprises a therapeutically effective amount of at least one compound of formula (I).

In another aspect, the invention provides a use of a compound of formula (I) for the manufacture of a medicament to treat disorders associated with LpxC.

The compounds of formula I have antibacterial activity and can be useful in the treatment of a microbial infection, including gram negative and gram positive infections.

In another aspect, the invention provides a method of preparing a pharmaceutical composition for treating the disorders associated with LpxC, said method comprising bringing into intimate contact at least one compound of formula and at least one pharmaceutically acceptable carrier.

In another aspect, the invention provides a pharmaceutical composition for treating disorders associated with LpxC, in a subject comprising, administering to the subject in need of such treatment a therapeutically effective amount of a compound of formula I or a pharmaceutically acceptable salt, solvate, ester or isomer thereof.

In another aspect, the invention provides a compound of formula I in purified form.

In another aspect, the invention provides a method of treating a condition or disease mediated by LpxC (such as a microbial infection), in a subject comprising: administering to the subject in need of such treatment a therapeutically effective amount of at least one compound of formula I or a pharmaceutically acceptable salt, solvate or isomer thereof.

In another aspect, the invention provides a method for the treatment of a microbial infection in a mammal, comprising administering to said mammal a therapeutically effective amount of a compound of formula I or a pharmaceutically acceptable salt, solvate or ester thereof. In one embodiment, the microbe causing the infection is a bacteria, in another embodiment it is a fungus. In one embodiment, the microbial infection is a gram negative infection; in another embodiment, it is a gram negative infection.

In another aspect, the invention provides a method for the treatment of a microbial infection in a mammal, comprising administering to said mammal a therapeutically effective amount of a compound of formula I in combination with one or more additional antibacterial or antifungal agent. In one embodiment, said additional antibacterial agent is active against gram negative bacteria. In another embodiment, said additional antibacterial agent is active against gram positive bacteria.

In one embodiment, the compounds of Formula (I) can be administered to a subject to treat gram negative bacterial infections. They may also be given along with other antibiotics, such as the macrolides, e.g., erythromycin, rifampicin and azithromycin, to achieve or enhance the gram negative antibacterial activity, or with other non-macrolide antibiotics to achieve or enhance the spectrum or potency of the particular antibacterial agent against gram negative organisms.

Likewise, the compounds of formula I can be used with other agents which are in and of themselves useful in conjunction with antibacterial agents. For example, bacterial cell wall permeabilizing agents can be included. Representative examples of such compounds include EDTA, polymixin B nonapeptide, poly-L-lysine and neomycin. Other permeability enhancing agents known to those skilled in the art can be included herein as well.

In another embodiment, the bacterial infection treatable by the compounds of the present invention is caused by at least one organism selected from the group consisting of *Acineto-* bacter baumannii, Acinetobacter calcoaceticus, Acinetobacter haemolyticus, Acinetobacter hydrophila, Actinobacillus actinomycetemcomitans, Aeromonas hydrophila, Alcaligenes xylosoxidans, Bacteroides distasonis, Bacteroides fragilis, Bacteroides melaninogenicus, Bacteroides ovatus, Bacteroides thetaiotaomicron, Bacteroides vulgatus, Bartonella henselae, Bordetella pertussis, Branhamella catarrhalis, Brucella melitensis, Brucella abortus, Brucella canis, Burkholderia cepacia, Burkholderia mallei, Burkholderia pseudomallei, Campylobacter coli, Campylobacter fetus, Campylobacter jejuni, Citrobacter diversus, Citrobacter freundii, Citrobacter koseri, Coxiella burnetli, Edwarsiella tarda, Ehrlichia chafeenis, Eikenella corrondens, Enterobacter aerogenes, Enterobacter agglomerans, Enterobacter cloacae, Escherichia coli, Flavobacterium meningosepticum, Francisella tularensis, Fusobacterium spp., Haemophilus ducreyi, Haemophilus influenzae, Haemophilus parainfluenzae, Helicobacter pylori, Kingella kingae, Klebsiella oxytoca, Klebsiella ozaenae, Kiebsiella pneumoniae, Klebsiella rhinoscleromatis, Legionella pneumophila, Moraxella catarrhalis, Morganella morganii, Neisseria gonorrhoeae, Neisseria meningitides, Pasteurella multocida, Plesiomonas shigelloides, Porphyromonas asaccharolytica, Porphyromonas gingivalis, Prevotella bivia, Prevotella buccae, Prevotella corporis, Prevotella endodontalis, Prevotella intermedia, Prevotella melaninogenica, Prevotella oralis, Proteus mirabilis, Proteus myxofaciens, Proteus penner, Proteus vulgaris, Providencia alcalifaciens, Providencia rettgeri, Providencia stuarfii, Pseudomonas aeruginosa, Pseudomonas fluorescens, Ricketsia prowozekii, Salmonella enterica, Serratia marcescens, Shigella boydii, Shigella dysenteriae, Shigella flexneri, Shigella sonnei, Stenotrophomonas maltophilia, Streptobacillus moniliformis, Vibrio alginolyticus, Vibrio cholerae, Vibrio parahaemolyticus, Vibrio vuluificus, Yersinia enterocolitica, Yersinia pestis, and Yersinia pseudotuberculosis.

In another embodiment, the bacterial infection is caused by at least one organism selected from the group consisting of Acinetobacter baumannii, Acinetobacter spp., Aeromonas hydrophila, Bacteroides fragilis, Bacteroides spp., Bordetella pertussis, Campylobacter jejuni, Campylobacter spp. Citrobacter freundii, Citrobacter spp., Enterobacter cloacae, Enterobacter spp., Escherichia coli, Fusobacterium spp., Haemophilus influenzae, Haemophilus parainfluenzae, Helicobacter pylori, Klebsiella pneumoniae, Klebsiella spp., Legionella pneumophila, Moraxella catarrhalis, Morganella morganii, Neisseria gonorrhoeae, Neisseria meningitides, Pasteurella multocida, Prevotella spp., Proteus mirabilis, Proteus spp., Providencia stuarti, Pseudomonas aeruginosa, Pseudomonas spp., Salmonella enterica, Salmonella typhi, Serratia marcescens, Shigella spp., Stenotrophomonas maltophilia, Vibrio cholerae, Vibrio spp., and Yersinia spp.

The standard LpxC assay consists of 0.2 nM LpxC enzyme, 1.0 µM UDP-3-O—(R-3-hydroxymyristoyl)-N-acetylglucosamine, and test compound, in assay buffer and 2% DMSO. Assay buffer is comprised of 25 mM HEPES, pH 7.3, 150 mM NaCl, 2.0 mM DTT, and 0.01% BSA. The enzyme reaction is carried out in a 96-well assay plate, in a final volume of 102 µL. Solutions of test compounds are prepared in 100% DMSO. Reaction additions, in order, are (1) 2.0 µL compound solution, (2) 80 µL of assay buffer, (3) 10 µL of 10 µM UDP-3-O—(R-3-hydroxymyristoyl)-N-acetylglucosamine (in assay buffer) and, (4) 10 µL of LpxC enzyme (20 nM in assay buffer) to initiate the reaction. In positive control reactions, addition (1) has 2.0 µL of 100% DMSO (without compound); these reactions are used as the total signal (TSB) value. Reactions are incubated at room temperature for 60 minutes when 10 µL of 1 N HCl is added to stop the reaction. The plate is shaken by hand for 10 seconds to ensure complete quenching. Assay plates are sealed with foil tape, and stored at −80° C. for 24-48 hr prior to analysis.

The concentrations of substrate and product in the reaction mixtures are determined with BioTrove's proprietary Rapid-Fire™ high-throughput mass spectrometry (HTMS). Assay mixtures are partially purified with reverse phase chromatography, where they are washed with water containing 5 mM ammonium formate and eluted onto the mass spectrometer in 80% acetonitrile, 20% water, and 5 mM ammonium formate. The mass spectrometry peak areas of the substrate and product are measured to determine the concentration of these analytes. The assay signal is the percentage of substrate that is converted to product. Percent inhibition, % I, in test samples is determined from the following equation:

$$\% I = 100 * \frac{(TSB - SampleSignal)}{(TSB)}.$$

Inhibitory activities of representative compounds of the present invention are set forth in the table below. In this table below, greater than 30% inhibition is assigned a rating of "A", 10-30% inhibition is assigned a rating of "B", and less than 10% inhibition is assigned a rating of "C".

| Compound # | Structure | LpxC enzyme assay rating (% inhibition at indicated concentrations of 100 and 25 ug/mL) | |
|---|---|---|---|
| | | 100 | 25 |
| 32 | 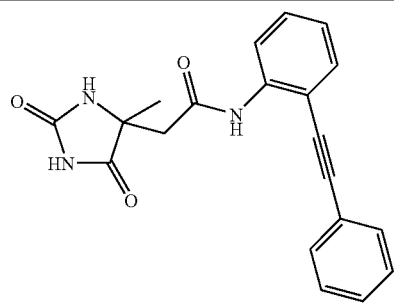 | | C |

-continued
| Compound # | Structure | LpxC enzyme assay rating (% inhibition at indicated concentrations of 100 and 25 ug/mL) | |
|---|---|---|---|
| | | 100 | 25 |
| 34 | 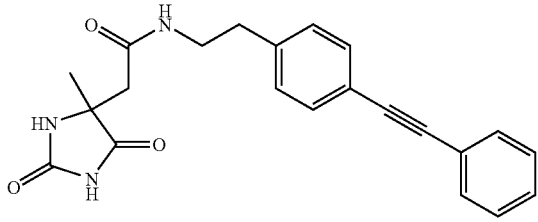 | | B |
| 35 | 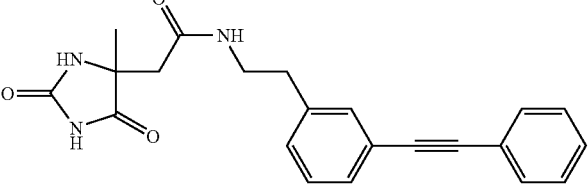 | | C |
| 41 | 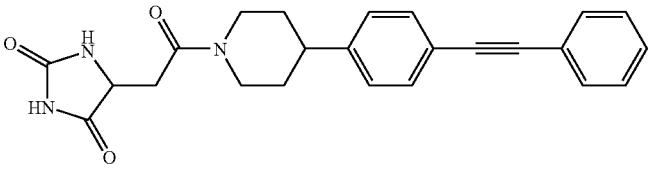 | | A |
| 42 | 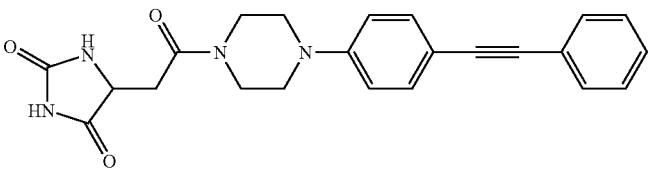 | | A |
| 45 | 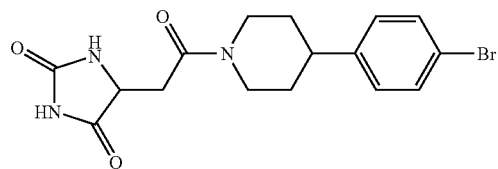 | | A |
| 46 | 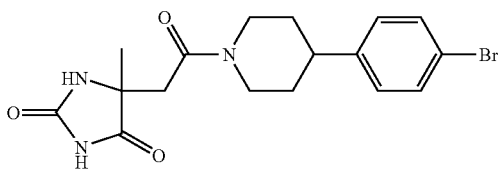 | | A |
| 47 | 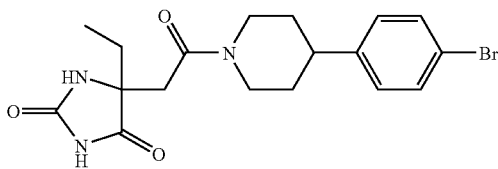 | | A |

Numerical LpxC inhibitory activities (% inhibition at indicated concentrations of 100 and 25 ug/mL) of representative compounds are shown in the table below.

| Compound # | Structure | LpxC enzyme assay rating (% inhibition at indicated concentrations of 100 and 25 ug/mL) | |
|---|---|---|---|
| | | 100 | 25 |
| 34 | *structure* | | 30 |
| 41 | *structure* | | 60 |
| 45 | *structure* | | 68 |

LpxC inhibitory activities ($IC_{50}$) for representative compounds are also shown in the table below. Compounds possessing $IC_{50}$ values greater than 5 μM (>5 μM) are designated as "D" class. Compounds possessing $IC_{50}$ values greater than 1 μM but up to 5 μM (>0.1 μM-5 μM) are designated as "C" class. $IC_{50}$ values between 0.25 μM to 1.0 μM (0.25 μM 1 μM) are designated as "B" class. $IC_{50}$ values less than 0.25 μM (<0.25 μM) are designated as "A" class.

| Compound # | Structure | $IC_{50}$ rating |
|---|---|---|
| 33 | *structure* | D |
| 36 | *structure* | B |

| Compound # | Structure | IC$_{50}$ rating |
|---|---|---|
| 37 | 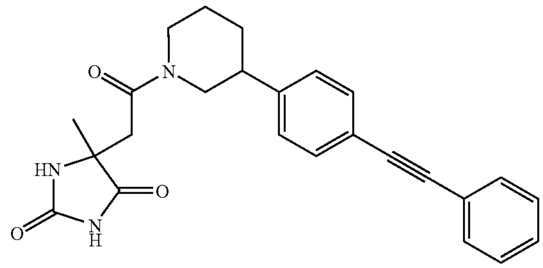 | B |
| 38 | 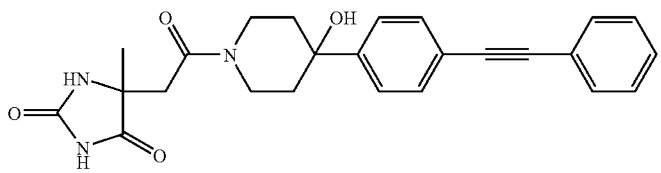 | C |
| 39 | 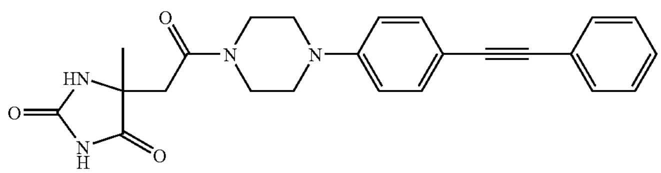 | B |
| 40 | 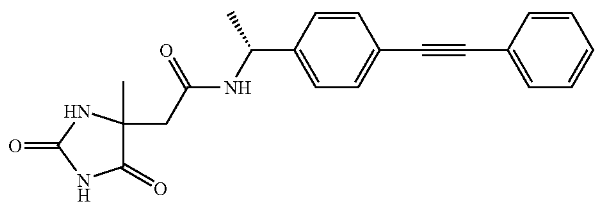 | D |
| 43 | 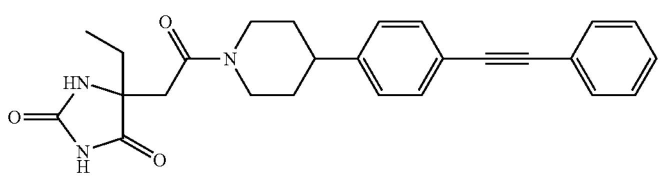 | B |
| 64 | 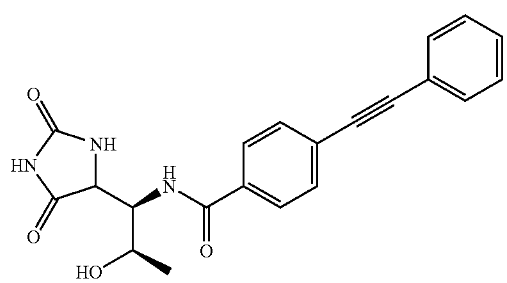 | D |
| 65 | 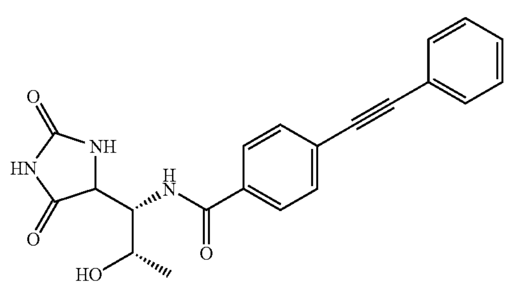 | D |

-continued

| Compound # | Structure | IC$_{50}$ rating |
|---|---|---|
| 66 | 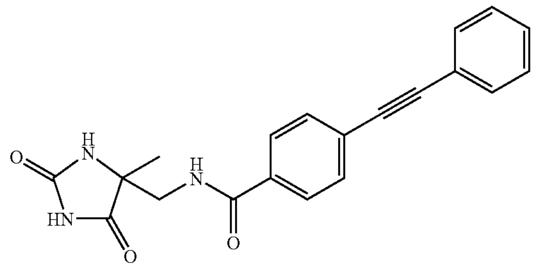 | D |
| 75 | 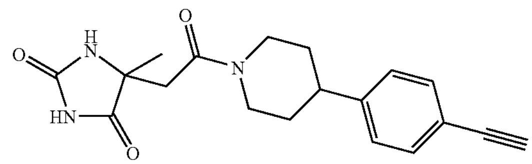 | D |
| 76 | 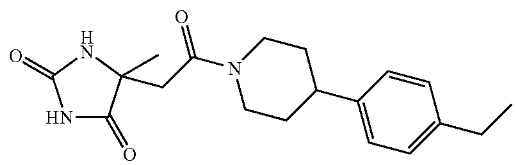 | D |
| 77 | 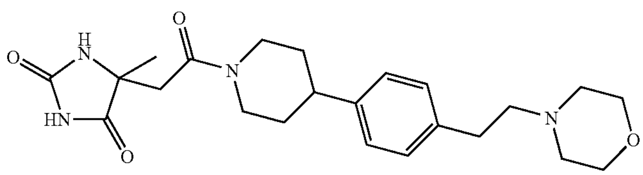 | D |
| 78 | 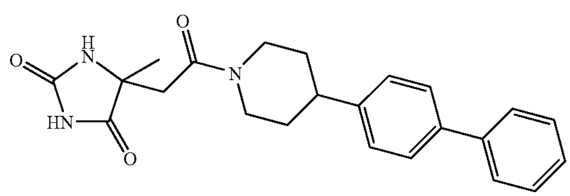 | D |
| 79 | 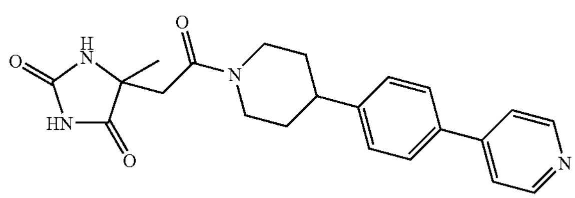 | D |

Numerical LpxC inhibitory activities (IC$_{50}$ values) of representative compounds are shown in the table below:

| Compound # | Structure | IC$_{50}$ values (μM) |
|---|---|---|
| 36 | 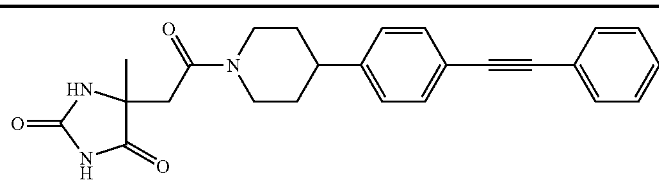 | 0.6 |

-continued

| Compound # | Structure | IC$_{50}$ values (µM) |
|---|---|---|
| 39 | 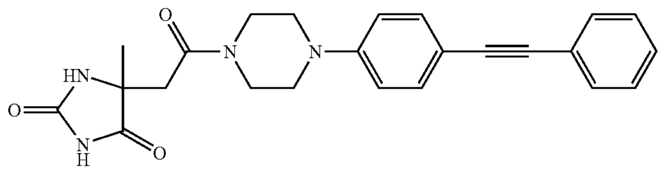 | 0.5 |
| 43 | 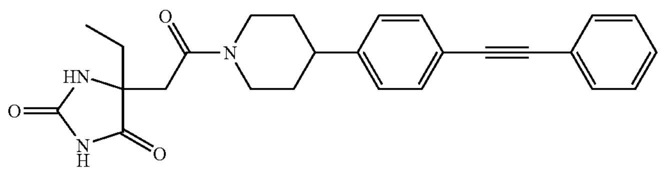 | 0.7 |

The pharmaceutical compositions containing the active ingredient may be in a form suitable for oral use, for example, as tablets lozenges aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256, 108; 4,166,452; and 4,265,874 to form osmotic therapeutic tablets for controlled release.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g. sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of The invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formula I useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations are used in the procedures and schemes:
ACN Acetonitrile
AcOH Acetic acid
ADDP 1,1$^1$-(Azodicarbonyl)dipiperidine
Anh. Anhydrous
Aq Aqueous
BOC tert-Butoxycarbonyl
° C. degrees Celsius
CBZCl Benzyl chloroformate
CDI Carbodiimide
DBU 1,8-Diazabicyclo[5.4.0]undec-7-ene
DCC Dicyclohexylcarbodiimide
DCM Dichloromethane
DEAD Diethyl azodicarboxylate
(DHQ)2PHAL Hydroquinine 1,4-phthalazinediyl diether
DIAD Diisopropylazodicarboxylate
DIEA Diisopropylethylamine
DMA N5N-Dimethylacetamide
DMAP 4-Dimethylaminopyridine
DME Dimethoxyethane
DMF Dimethylformamide
DMFDMA N,N-Dimethylformamide dimethylacetal
DMPU 1,3-Dimethyl-3,4,5,6-tetrahydro-2(1h)-pyrimidinone
DMSO Dimethyl sulfoxide
EDC 1-(3-Dimethylaminopropyl)-3-ethylcarbodiimide hydrochloride
EI Electron ionization
Eq Equivalents
EtOAc Ethyl acetate
ETOH Ethanol
g grams
h. hours
$^1$H proton
HATU N,N,N',N'-Tetramethyl-O-(7-Azabenzotriazol-1-yl) Uronium hexafluorophosphate
Hex hexanes
HOBt 1-Hydroxybenzotriazole
HPLC High pressure liquid chromatography
LAH Lithium aluminum hydride
LDA Lithium diisopropylamide
M Molar
mCPBA meta-Chloroperoxybenzoic acid
Me Methyl
MeCN Acetonitrile
MeOH Methanol
min Minutes
mg Milligrams
MHz Megahertz
ml Milliliter
MS Mass Spectroscopy
NMM N-Methylmorpholine
NMP 1-methyl-2-pyrrolidone ON Overnight
Pd(tBu3P)2 Bis-(tri-tert-butylophosphine)palladium
Pd(TPP)4 Tetrakis-(triphenylphosphine)palladium
Pd(OaC)2 Palladium(II) acetate
PdCl2(TPP)2 Bis-(triphenylphosphine)palladium(II) chloride
PdCl2(ddppf) Dichloro[1,1'-bis(diphenylphosphino)ferrocene]palladium(ii) dichloride
Pd2(dba)3 Tris(dibenzylideneacetone)dipalladium(0)
PyBrOP Bromo-trispyrrolidino-phosphonium hexafluorophosphate
Pyr Pyridine
RT Room temperature
SiO2 Silica gel 60 chromatography
sgc Silica get 60 chromatography
tBOC tert-Butoxycarbonyl
TACE TNF-alpha converting enzyme
TEA Triethylamine
TFA Trifluoroacetic acid
THF Tetrahydrofuran
TLC Thin layer chromatography
TPP Triphenylphosphine
$t_R$ Retention time NMR spectra were acquired on a Mercuryplus 400 MHz NMR Spectrometer (Varian), using CDCl3 or DMSO-d6 as solvents, LC-MS data was obtained using an Agilent 1100 Series LC/MSD (quadrupole, API-ES (Atmospheric Pressure Interface Electrospray)) with a capillary voltage set to 3500 V and running in positive mode. Reported analytical HPLC (LC/MS) retention times were obtained using a C18 (150×4.6 mm) reverse-phase column eluting with a 5 or 10 minute gradient of 0.1% trifluoroacetic acid in water to 95:5 acetonitrile:water at a flow rate of 3 mL/min.

Purification via reverse phase chromatography was accomplished using a C18 reverse phase column with a gradient of 0.1% trifluoroacetic acid in water to 95:5 acetonitrile:water at a flow rate of 20 mL/min. Samples were collected using a UV (Gilson, 254 nm) or mass spectra (Agilent 1100 Series LC/MSD model SL) signal.

Normal phase silica gel chromatography on a Biotage instrument was accomplished using a Quad UV System (P/N 07052) utilizing KP-SIL 32-63 um columns, 60 Å with flash cartridges 12+M or 25+M.

The compounds of formula (I) may be produced by processes known to those skilled in the art and as shown in the following reaction schemes and in the preparations and examples described below. These preparations and examples should not be construed to limit the scope of the disclosure. Alternate mechanistic pathways and analogous structures may be apparent to those skilled in the art. All kinds of isomeric forms of the compounds are considered to be within the scope of this invention.

EXAMPLES

Example 1

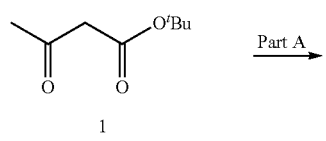

1

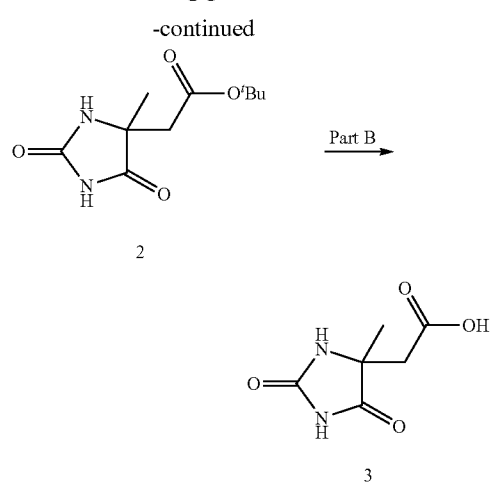

Part A:

tert-Butylacetoacetate (1) (1.66 mL, 10 mmol), ammonium carbonate (3.36 g, 35 mmol) and potassium cyanide (0.98 g, 15 mmol) in ethanol (10 mL) and water (10 mL) was heated at 75° C. for 18 hours in a sealed pressure tube. The reaction mixture was cooled to room temperature and the volatiles were removed in vacuo. The residue was re-dissolved in ethyl acetate (20 mL), washed with water (20 mL), separated and dried over magnesium sulfate. Concentration afforded compound 2 as a white solid (1.12 g, 50% yield). HPLC-MS $t_R$=0.95 min (UV$_{254\,nm}$); mass calculated for formula $C_{10}H_{16}N_2O_4$ 228.1, observed LCMS m/z 173.1 (M+H—$^t$Bu).

Part B;

To a solution of compound 2 (0.1 mmol) in dioxane (1 mL) at 0° C. (ice-bath) was added 4 N HCl in dioxane (2 mL) and water (0.2 mL). The reaction mixture was stirred at room temperature for 3 hours. LC-MS analysis of the reaction indicated that the reaction was complete. The volatiles were removed in vacuo, acetonitrile was added, concentrated and dried to afford compound 3 as a white solid (100% yield). HPLC-MS $t_R$=0.21 min (UV$_{254\,nm}$); mass calculated for formula $C_6H\,N_2O_4$ 172.1, observed LCMS m/z 173.1 (M+H).

Example 2

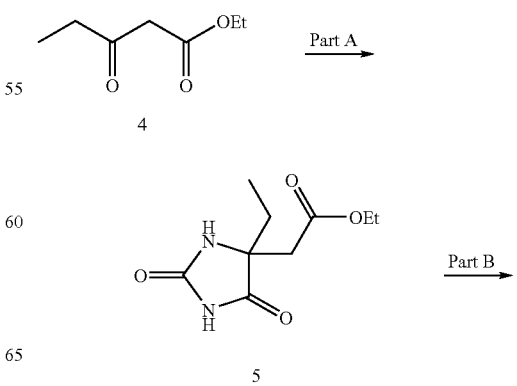

-continued

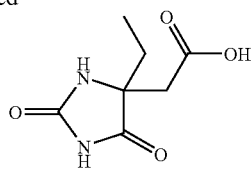

6

Part A:

Compound 5 was prepared from ethyl propionylacetate (4) using the hydantoin forming conditions described in Example 1, Part A. $^1$H NMR (400 MHz, DMSO): δ 0.74 (CH$_2$CH$_3$, t, 3H), 1.13 (OCH$_2$CH$_3$, t, 3H), 1.54 (CH$_2$CH$_3$, m, 2H), 2.49 (CH$_2$CO$_2$, d, 1H), 2.76 (CH$_2$CO$_2$, d, 1H), 4.00 (OCH$_2$CH$_3$, m, 2H), 7.82 (NHCO, s, 1H), 10.61 (CONHCO, s, 1H).

Part B:

A solution containing compound 5 (250 mg, 1.2 mmol) and lithium hydroxide (1M, 1.75 mL, 1.75 mmol) in THF (5 mL) and water (3 mL) was heated at 55° C. for 18 hours. LC-MS analysis of the reaction indicated that the hydrolysis was complete. The reaction mixture was acidified to pH 4.0 with 1N HCl, and the crude product extracted into ethyl acetate (2×10 mL). Drying over magnesium sulfate, and concentration afforded compound 6 as a white solid (100% yield). $^1$H NMR (400 MHz, DMSO): δ 0.74 (CH$_2$CH$_3$, t, 3H), 1.53 (CH$_2$CH$_3$, m, 2H), 2.43 (CH$_2$CO$_2$, d, 1H), 2.68 (CH$_2$CO$_2$, d, 1H), 7.77 (NHCO, s, 1H), 10.53 (CONHCO, s, 1H), 12.36 (CO$_2$H, s, 1H).

Example 3

Example 3A

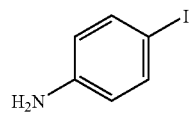

7

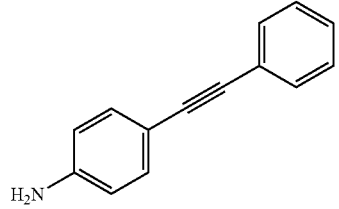

8

Part A:

To a mixture of 4-iodoaniline (7) (440 mg, 2 mmol), copper iodide (7.6 mg, 0.04 mmol) and dichlorobis(triphenylphosphine)palladium (II) (14 mg, 0.02 mmol) in THF (5 mL) was added phenylacetylene (244.8 mg, 2.4 mmol) and triethylamine (556 μL, 4 mmol). The reaction vessel was flushed with argon, and the reaction mixture stirred at room temperature for 18 hours. LC-MS analysis of the reaction indicated that the reaction was complete. Ethyl acetate (5 mL) was added, and the precipitates removed by passing through a plug of celite. The filtrate was concentrated, and the crude purified by flash column chromatography (SiO$_2$, 6% ethyl acetate in hexanes) to afford compound 8 as a brown solid (321 mg, 82% yield). HPLC-MS t$_R$=1.88 min (UV$_{254\ nm}$), mass calculated for formula C$_{14}$H$_{11}$N 193.1, observed LCMS m/z 194.1 (M+H).

Example 3B

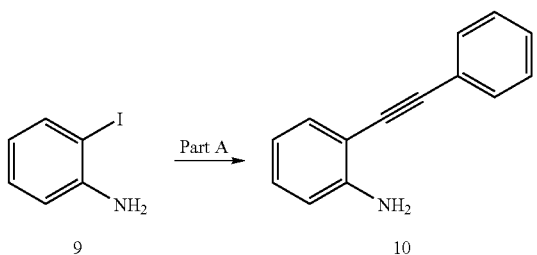

Part A:

Compound 10 was prepared from 2-iodoaniline (9) using the Sonogashira coupling conditions described in Example 3A, Part A. HPLC-MS t$_R$=2.01 min (UV$_{254\ nm}$); mass calculated for formula C$_{14}$H$_{11}$N 193.1, observed LCMS m/z 194.1 (M+H).

Example 3C

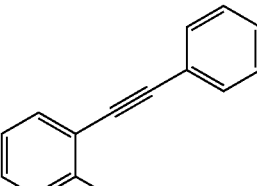

11

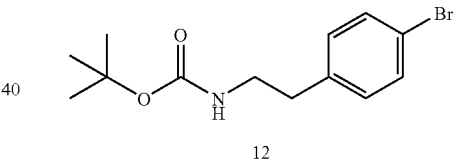

12

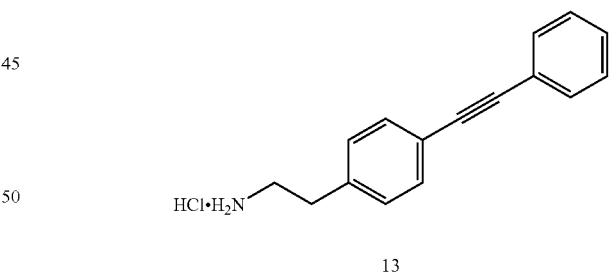

13

Part A:

A mixture of 4-bromophenethylamine (11) (0.5 g, 2.5 mmol, and di-tert-butyl dicarbonate (0.65 g, 3 mmol) at 0° C. in DCM (5 mL) was warmed to room temperature and stirred for 3 hours. LC-MS analysis indicated the reaction was complete. Dichloromethane (5 mL) was added and the solution washed with 1N HCl (10 mL). Drying over magnesium sulfate, concentration and purification by flash column chromatography (SiO$_2$, 12.5% ethyl acetal in hexanes) afforded compound 12 as a white solid (0.68 g, 91% yield). HPLC-MS t$_R$=2.13 min (UV$_{254\ nm}$); mass calculated for formula C$_{13}$H$_{18}$BrNO$_2$ 299.1, observed LCMS m/z 244.1 (M+H—$^t$Bu).

Part B:

A solution of compound 12 (139 mg, 0.46 mmol) in acetonitrile (2 mL) was transferred to a Schlenk tube containing dichlorobis(acetonitrile)palladium (11) (1.2 mg, 4.6 μmol), X-Phos (6.6 mg, 14 μmol) and cesium carbonate (391 mg, 1.2 mmol) and the reaction mixture was stirred at room temperature under an inert atmosphere for 25 minutes. 100 μL of a solution containing phenylacetylene (61.2 mg, 0.6 mmol) in acetonitrile (1 mL) was added and the reaction mixture heated at 90° C. for 15 minutes. The phenylacetylene solution (100 μL) was added every 15 minutes and the reaction mixture was heated at 90° C. for a total of 2.5 hours. LC-MS analysis indicated the reaction was complete. Water (3 mL) was added and the crude product extracted into ethyl acetate (5 mL). Drying over magnesium sulfate, concentration and purification by flash column chromatography (SiO$_2$, 12.5% ethyl acetate in hexanes) afforded BOC-protected compound 13 as a yellow solid (114 mg, 77% yield). HPLC-MS $t_R$=2.42 min (UV$_{254\ nm}$); mass calculated for formula C$_{21}$H$_{23}$NO$_2$ 321.2, observed LCMS m/z 266.2 (M+H—$^t$Bu).

The BOC-protecting was hydrolyzed using the conditions described in Example 1, Part B. HPLC-MS $t_R$=0.99 min (UV$_{254\ nm}$); mass calculated for formula C$_{16}$H$_{15}$N 221.1, observed LCMS m/z 222.2 (M+H).

Example 3D

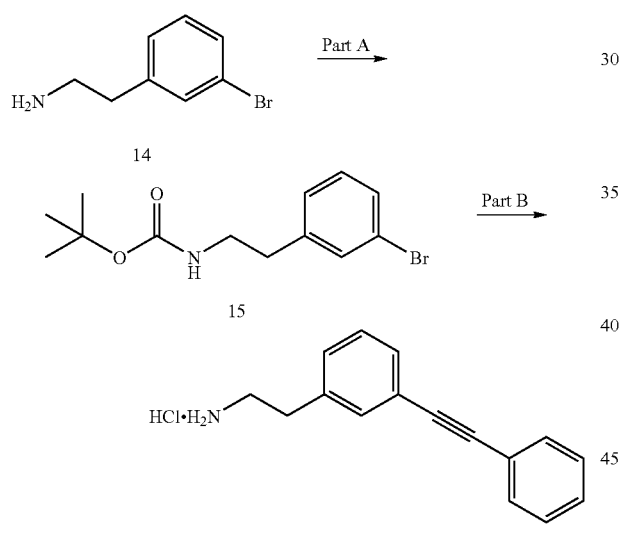

Compound 16 was prepared from 3-bromophenethylamine (14) using the conditions described in Example 3C, Part A and Part B. HPLC-MS $t_R$=1.18 min (UV$_{254\ nm}$); mass calculated for formula C$_{16}$H$_{15}$N 221.1 observed LCMS m/z 222.1 (M+H).

Example 3E

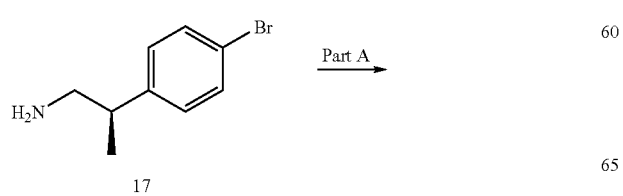

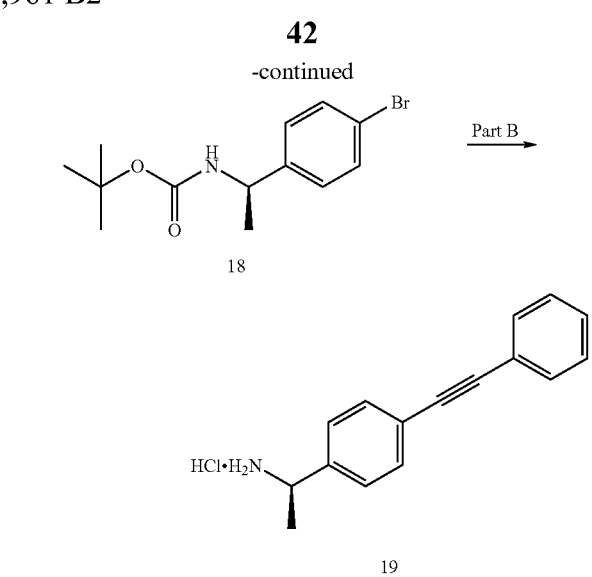

Compound 19 was prepared from (R)-(+)-4-bromo-α-methylbenzylamine (17) using the conditions described in Example 3C, Part A and Part B. HPLC-MS $t_R$=1.19 min (UV$_{254\ nm}$): mass calculated for formula C H, N 221.1, observed LCMS m/z 205.1 (M+H—NH$_3$).

Example 3F

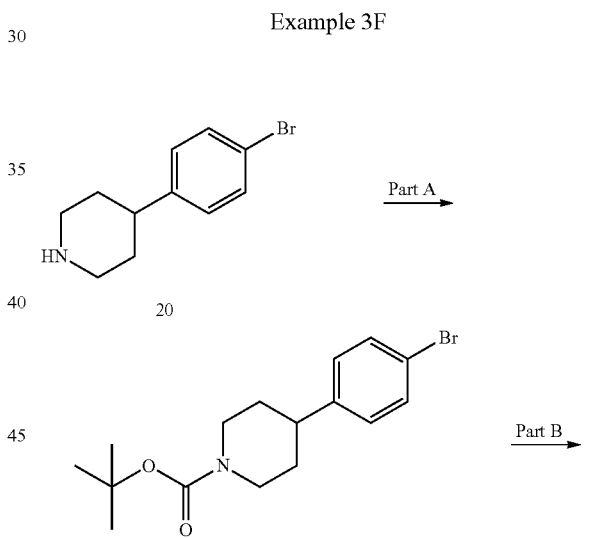

Compound 22 was prepared from 4-(4-bromophenyl)piperidine (20) using the conditions described in Example 3C, Part A and Part B. HPLC-MS $t_R$=1.22 min (UV$_{254\ nm}$); mass calculated for formula C$_{19}$H$_{19}$N 261.2, observed LCMS m/z 262.2 (M+H), Example 3G

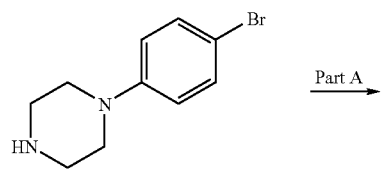

23

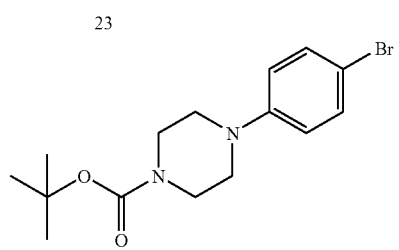

24

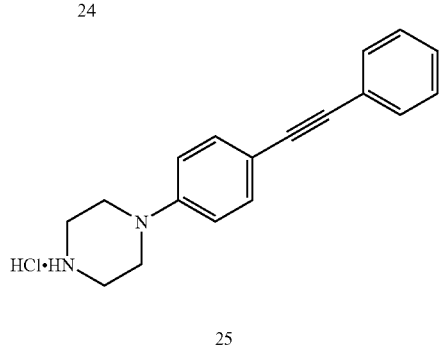

25

Compound 25 was prepared from 1-(4-bromophenyl)piperazine (23) using the conditions described in Example 3C, Part A an Part B HPLC-MS $t_R$=1.19 min (UV$_{254\ nm}$) mass calculated for formula C$_{18}$H$_{18}$N$_2$ 262.2, observed LCMS m/z 263.1 (M+H)

Example 3H

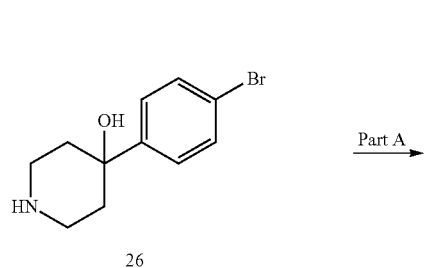

26

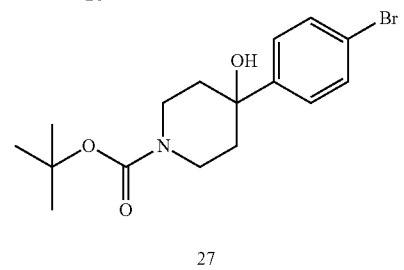

27

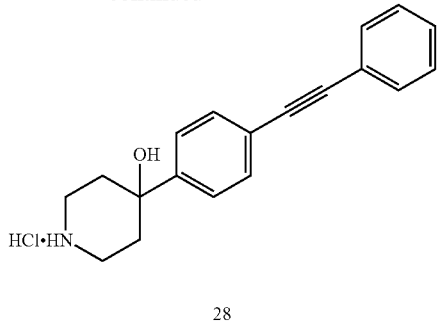

28

Compound 28 was prepared from 4-(4-bromophenyl)-4-piperidinol (26) using the conditions described in Example 3C, Part A and Part B. HPLC-MS $t_R$=1.09 min (UV$_{254\ nm}$); mass calculated for formula C$_{19}$H$_{19}$NO 277.2, observed LCMS m/z 278.1 (M+H).

Example 3I

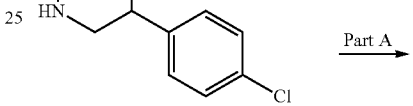

29

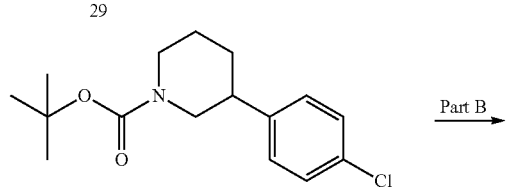

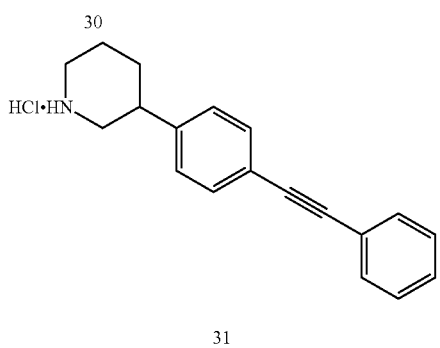

31

Compound 31 was prepared from 3-(4-chlorophenyl)piperidine (29) using the conditions described in Example 3C, Part A and Part B. HPLC-MS $t_R$=1.28 min (UV$_{254\ nm}$); mass calculated for formula C$_{19}$H$_{19}$N 261.2, observed LCMS m/z 262.2 (M+H).

Example 4

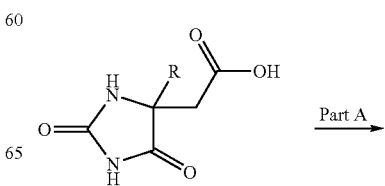

-continued

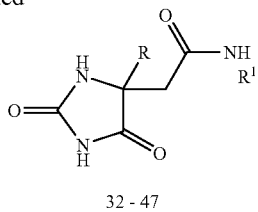
32-47

Part A:

To a solution of monoacid (3, 6, or 5-hydantoinacetic acid) (0.12 mmol) and HATU (68 mg, 0.18 mmol) in DMF (2 mL) was added amine building block (1.2 equivalents) and diisopropylethylamine (69 µL, 0.40 mmol). The reaction mixture was stirred at room temperature for 18 hours. LC-MS analysis of the reaction indicated that the reaction was complete. The volatiles were removed in vacuo, ethyl acetate was added, and the organic solution washed successively with saturated NaHCO$_3$ (×1), water (×1), brine (×1), dried over magnesium sulfate and concentrated. Purification by Prep. LC afforded compounds 32-47 (80-90% yield).

The following compounds were synthesized using this procedure:

| Serial # | Structure | Exact mass | MS m/z (M$^+$ + H) | Ret. Time (min) |
|---|---|---|---|---|
| 32 | 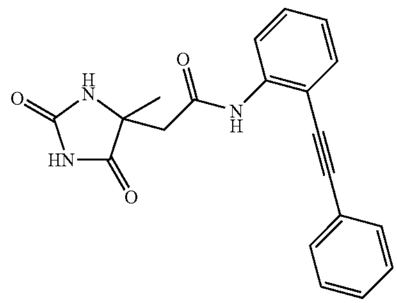 | 347.1 | 348.1 | 4.19 |
| 33 | 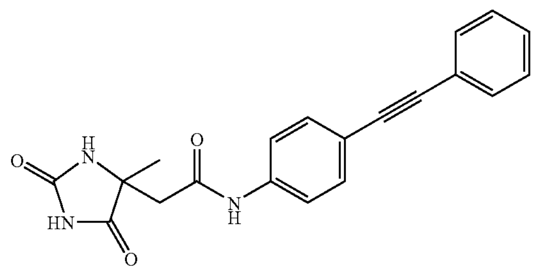 | 347.1 | 348.1 | 4.27 |
| 34 | 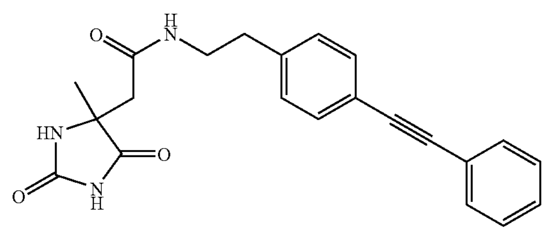 | 375.2 | 376.1 | 4.46 |
| 35 | 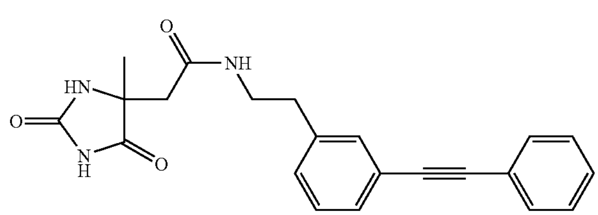 | 375.2 | 376.1 | 4.45 |
| 36 | 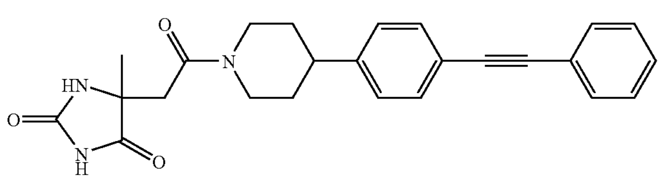 | 415.2 | 416.1 | 5.07 |

-continued

| Serial # | Structure | Exact mass | MS m/z (M+ + H) | Ret. Time (min) |
|---|---|---|---|---|
| 37 | 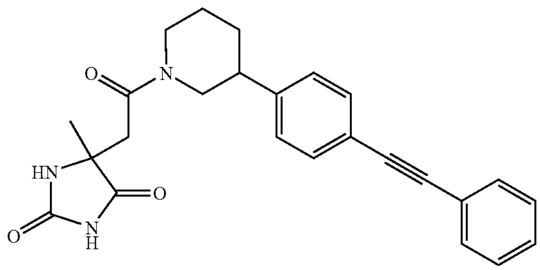 | 415.2 | 416.1 | 5.11 |
| 38 | 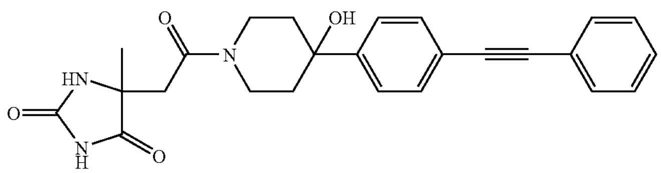 | 431.2 | 432.1 | 4.30 |
| 39 | 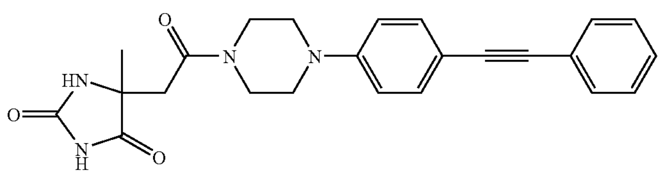 | 416.2 | 417.1 | 4.75 |
| 40 | 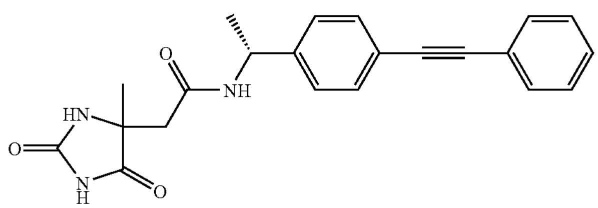 | 375.2 | 376.2 | 4.44 |
| 41 | 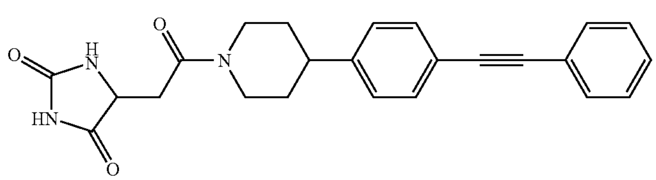 | 401.2 | 402.1 | 5.05 |
| 42 | 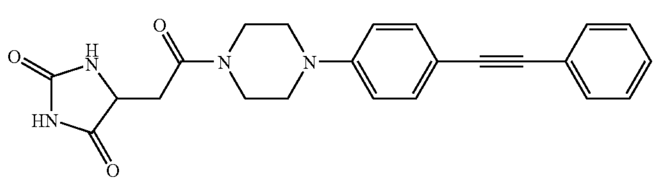 | 402.2 | 403.1 | 4.72 |
| 43 | 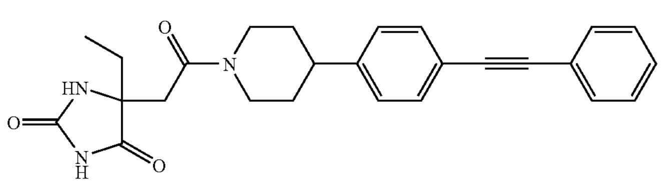 | 429.2 | 430.1 | 4.78 |

-continued

| Serial # | Structure | Exact mass | MS m/z (M⁺ + H) | Ret. Time (min) |
|---|---|---|---|---|
| 44 | 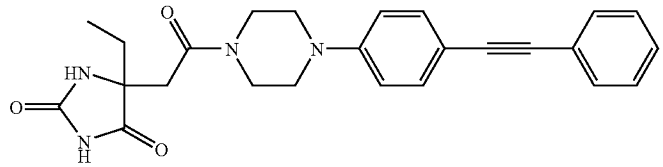 | 430.2 | 431.1 | 4.86 |
| 45 | 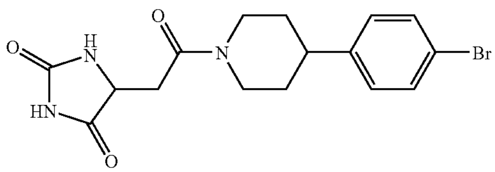 | 379.1 | 380.1 | 3.98 |
| 46 | 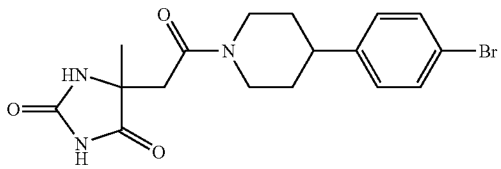 | 393.1 | 394.1 | 4.06 |
| 47 | 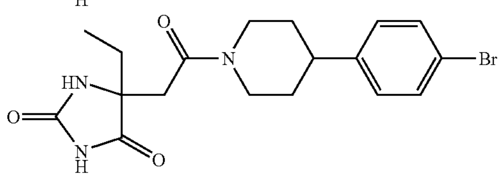 | 407.1 | 408.1 | 4.23 |

Example 5

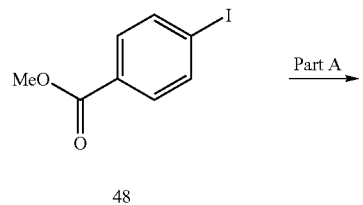

Part A:

Compound 49 was prepared from methyl 4-iodobenzoate (48) using the Sonagashira coupling conditions described in Example 3A, Part A. $^1$H NMR (400 MHz, DMSO): δ 3.85 (OCH$_3$, s, 3H), 7.44 (Phe CH, m, 3H), 7.58 (Phe CH, dd, 2H), 7.68 (Phe CH, d, 2H), 7.97 (Phe CH, d, 2H).

Part B:

Compound 50 was prepared from compound 49 using the saponification conditions described in Example 2, Part B. $^1$H NMR (400 MHz, DMSO): δ 7.43 (Phe CH, m, 3H), 7.58 (Phe CH, dd, 2H), 7.65 (Phe CH, d, 2H), 7.95 (Phe CH, d, 2H).

Example 6

Example 6A

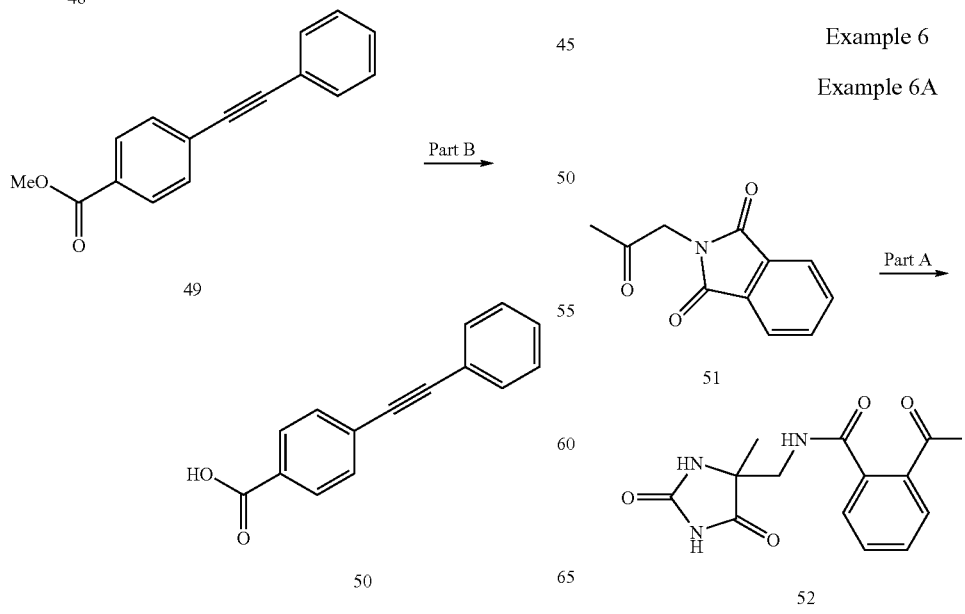

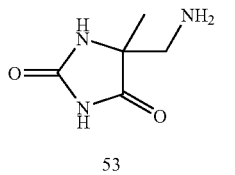

53

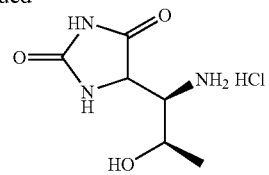

58

Part A:

Compound 52 was prepared from phthalimidoacetone (51) using the hydantoin forming conditions described in Example 1, Part A. HPLC-MS $t_R$=0.62 nm (UV$_{254\ nm}$); mass calculated for formula $C_{13}H_{13}N_3O_5$ 291.1 observed LCMS m/z 292.1 (M+H).

Part B:

A solution containing compound 52 (100 mg, 0.34 mmol) and 6N HCl (5 mL) was heated at 100° C. for 18 hours. LC-MS analysis of the reaction indicated that the hydrolysis was complete. The volatiles were removed in vacuo, and the resulting residue triturated with diethyl ether to afford compound 53 as a white solid (55 mg, 89% yield). HPLC-MS $t_R$=0.20 min (UV$_{254\ nm}$); mass calculated for formula $C_5H_9N_3O_2$ 143.1, observed LCMS m/z 144.1 (M+H).

Example 6B

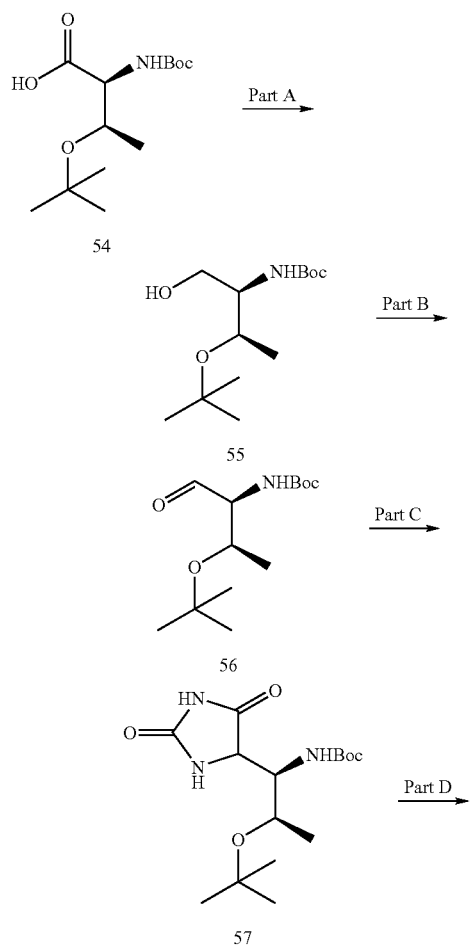

Part A:

To a cooled solution of borane-THF (1M, 4 mL, 4 mmol) at 0° C., was added drop-wise over 30 minutes a solution containing boc-L-thr($^t$Bu)—OH (551 mg, 2 mmol) in THF (2 mL). The reaction mixture was stirred at 0° C. for an additional hour. LC-MS analysis of the reaction indicated that the reduction was complete. Excess borane was quenched by the addition of acetic acid (10% in methanol, 10 mL). The volatiles were removed in vacuo. The resulting residue was dissolved in ethyl acetate (20 mL), and washed successively with 1N HCl (×1) water (×1) and saturated NaHCO$_3$ (×1). Drying over magnesium sulfate and concentration afforded compound 55 as a colorless oil (387 mg, 74% yield). HPLC-MS $t_R$=1.71 min (UV$_{254\ nm}$), mass calculated for formula $C_{13}H_{27}NO_4$ 261.2, observed LCMS m/z 150.1 (M−(2×$^t$Bu)+H).

Part B:

A mixture of compound 55 (261 mg, 1 mmol) and Dess-Martin periodinane (466 mg, 1.1 mmol) in dichloromethane (20 mL) was stirred at room temperature for 18 hours. LC-MS analysis of the reaction indicated that the oxidation was complete. A saturated solution of NaHCO$_3$ (20 mL) containing sodium thiosulfate (1.1 g, 7 mmol) was added, and the reaction mixture stirred for an additional 10 minutes. The reaction mixture was diluted with dichloromethane (20 mL), the organics separated, dried over magnesium sulfate, and concentrated to afford compound 56 as a white solid (200 mg, 77% yield). HPLC-MS $t_R$=2.14 min (UV$_{254\ nm}$); mass calculated for formula $C_{13}H_{25}NO_4$ 259.2, observed LCMS m/z 148.1 (M−(2×$^t$Bu)+H).

Part C:

Compound 57 was prepared from compound 56 using the hydantoin forming conditions described in Example 1, Part A. HPLC-MS $t_R$=1.53 min (UV$_{254\ nm}$); mass calculated for formula $C_{15}H_{27}N_3O_5$ 329.2, observed LCMS m/z 174.1 (M+H−$^t$Bu-Boc).

Part D:

Compound 58 was prepared from compound 57 using the hydrolysis conditions described in Example 1, Part B. HPLC-MS $t_R$=0.20 min (UV$_{254\ nm}$); mass calculated for formula $C_6H_{11}N_3O_3$ 173.1, observed LCMS m/z 174.1 (M+H).

Example 6C

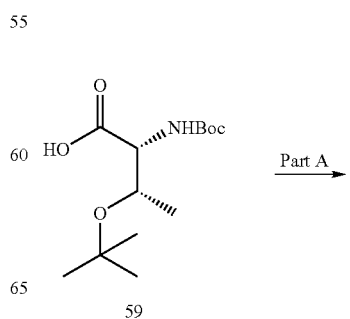

59

Part A

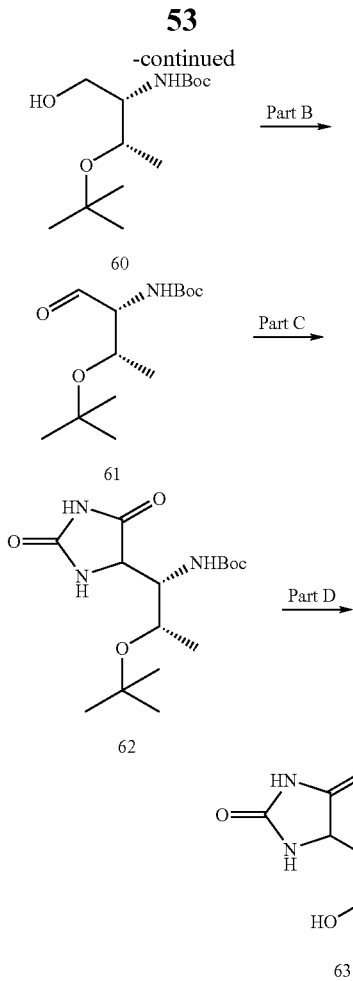

A. HPLC-MS $t_R$=1.61 min (UV$_{254}$ nm); mass calculated for formula $C_{15}H_{27}N_3O_5$ 329.27 observed LCMS m/z 174.1 (M+H—$^t$Bu-Boc).

Part D:

Compound 63 was prepared from compound 62 using the hydrolysis conditions described in Example 17 Part B. HPLC-MS $t_R$=0.21 min (UV$_{254\ nm}$); mass calculated for formula $C_6H_{11}N_3O_3$ 173.1, observed LCMS m/z 174.1 (M+H).

Example 7

Part A:

Compound 60 was prepared from compound 59 using the reduction conditions described in Example 6B, Part A. HPLC-MS $t_R$=1.81 min (UV$_{254\ nm}$); mass calculated for formula $C_{13}H_{27}NO_4$ 261.27 observed LCMS m/z 150.1 (M−(2×$^t$Bu)+H).

Part B:

Compound 61 was prepared from compound 60 using the oxidation conditions described in Example 68 Part B. HPLC-MS $t_R$=2.20 min (UV$_{254\ nm}$); mass calculated for formula $C_{13}H_{25}NO_4$ 259.2, observed LCMS m/z 148.1 (M−(2×$^t$Bu)+H).

Part C:

Compound 62 was prepared from compound 61 using the hydantoin forming conditions described in Example 1, Part Part A:

To a solution of amine (compounds 53, 58, and 63) (0.18 mmol) and HATU (86 mg, 0.23 mmol) in DMF (2 mL) was added compound 50 (54 mg, 0.24 mmol) and diisopropylethylamine (72 µL, 0.41 mmol). The reaction mixture was stirred at room temperature for 18 hours. LC-MS analysis of the reaction indicated that the reaction was complete. The volatiles were removed in vacuo, ethyl acetate was added, and the organic solution washed successively with saturated NaHCO$_3$ (×1), water (×1), brine (×1), dried over magnesium sulfate and concentrated. Purification by preparative LC afforded compounds 64-66 (80-90% yield).

The following compounds were synthesized using this procedure:

| Serial # | Structure | Exact mass | MS m/z (M$^+$ + H) | Ret. Time (min) |
|---|---|---|---|---|
| 64 | 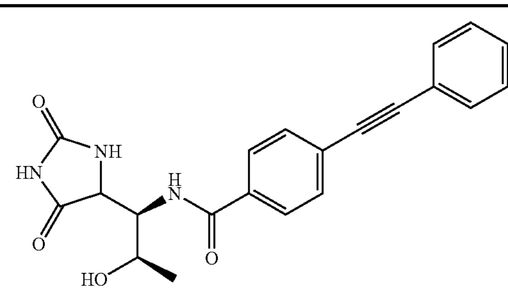 | 377.1 | 378.1 | 3.94 |

| Serial # | Structure | Exact mass | MS m/z (M⁺ + H) | Ret. Time (min) |
|---|---|---|---|---|
| 65 | 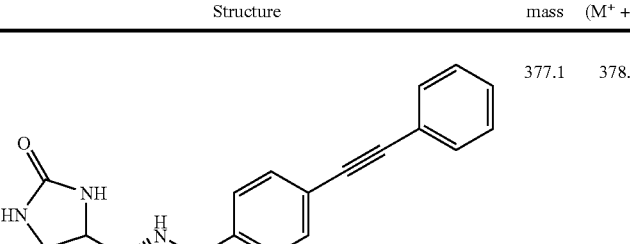 | 377.1 | 378.1 | 4.02 |
| 66 | 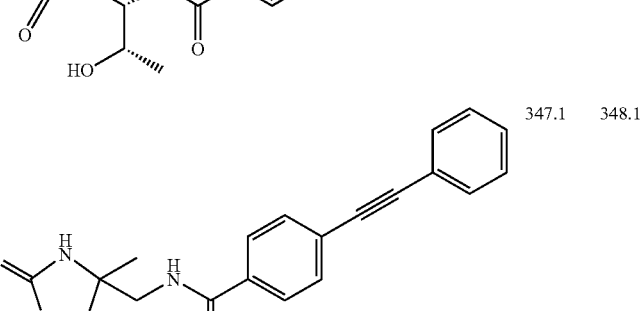 | 347.1 | 348.1 | 4.10 |

Example 8

Example 8A

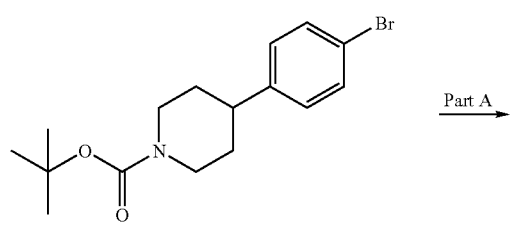

Part A:

Compound 67 was prepared from compound 21 using the conditions described in Example 3C, Part B, HPLC-MS $t_R$=2.81 min (UV$_{254\ nm}$); mass calculated for formula $C_{21}H_{31}NO_2Si$ 357.2, observed LCMS m/z 302.2 (M+H–$^t$Bu).

Part B:

To a solution of compound 67 (18 mg, 0.05 mmol) in THF (1 mL) was added tetrabutylammonium fluoride (1M solution in THF, 50 uL, 0.05 mmol). The reaction mixture was stirred at room temperature for 1 hour. LC-MS analysis of the reaction indicated that the reaction was complete. The volatiles were removed in vacuo, and the residue re-dissolved in ethyl acetate (2 mL), washed with ammonium chloride (2 mL), separated and dried over magnesium sulfate. Concentration and purification by flash column chromatography (SiO$_2$, 20% ethyl acetate in hexanes) afforded compound 67 as a colorless oil. HPLC-MS $t_R$=2.34 min (UV$_{254}$ n1); mass calculated for formula $C_{18}H_{23}NO_2$ 285.2, observed LCMS m/z 230.2 (M+H—$^t$Bu).

Part C:

Compound 69 was prepared from compound 68 using the hydrolysis conditions described in Example 1, Part B. HPLC-MS $t_R$=0.90 min (UV$_{254\ nm}$); mass calculated for formula $C_{13}H_{15}N$ 185.1, observed LCMS m/z 186.2 (M+H).

Example 8B

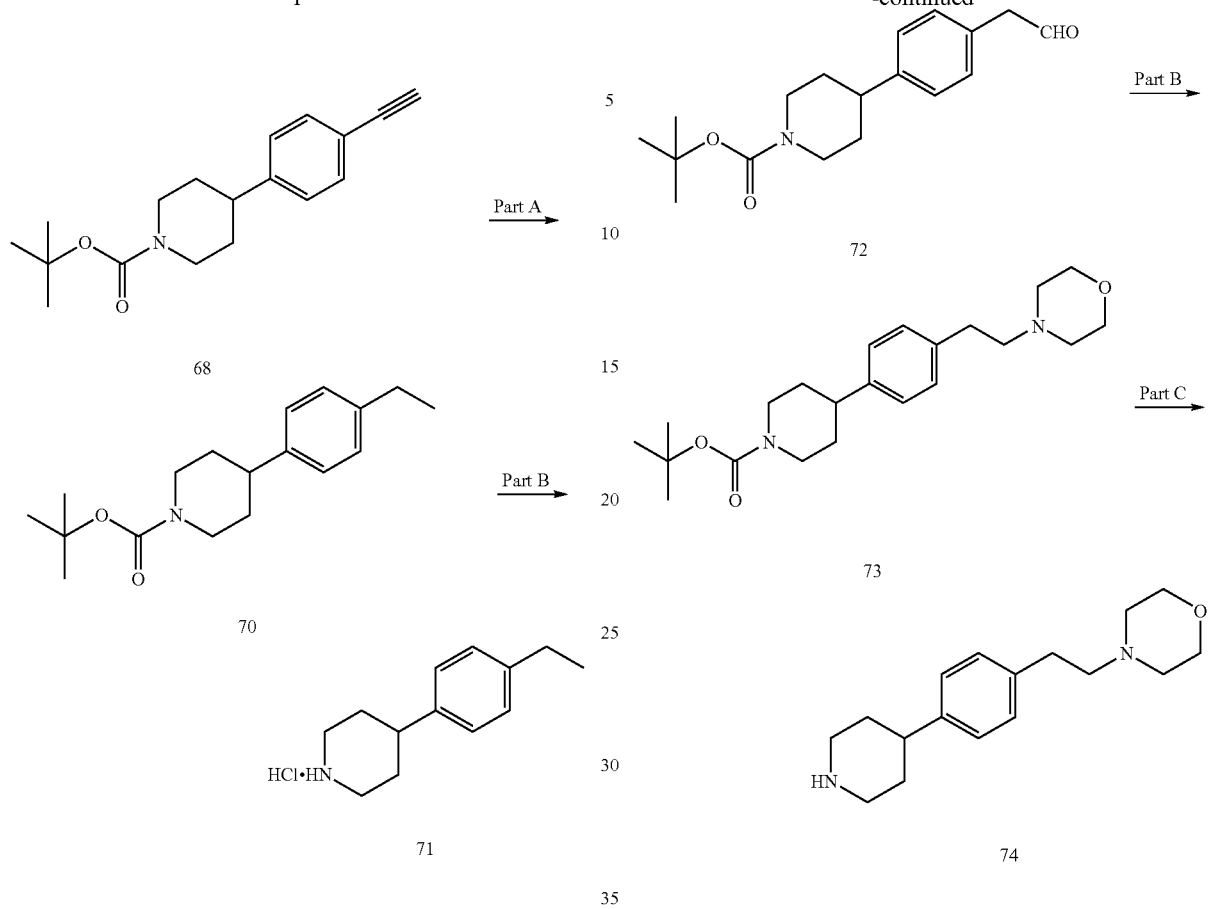

Part A:

To a solution of compound 68 (30 mg, 0.105 mmol) in ethyl acetate (3 mL) was added palladium on carbon (10%, 0.01 mmol) and the reaction mixture stirred under an $H_2$ atmosphere for 16 hours. LC-MS analysis of the reaction indicated that the reaction was complete. The precipitates were removed by passing through a plug of celite, and the filtrate evaporated to afford compound 70 as colorless oil. HPLC-MS $t_R$=2.56 min ($UV_{254\ nm}$); mass calculated for formula $C_{18}H_{27}NO_2$ 289.2, observed LCMS m/z 234.2 (M+H−$^t$Bu).

Part B:

Compound 71 was prepared from compound 70 using the hydrolysis conditions described in Example 1, Part B. HPLC-MS $t_R$=0.90 min ($UV_{254\ nm}$); mass calculated for formula $C_{13}H_{19}N$ 189.2, observed LCMS m/z 190.2 (M+H).

Example 8C

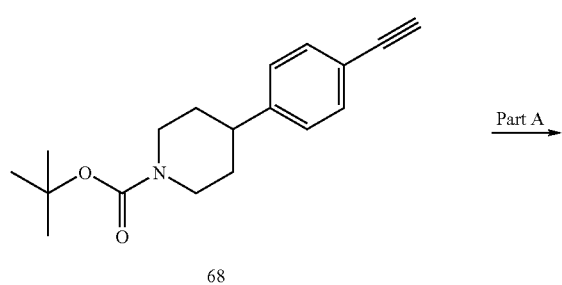

Part A:

To a solution of compound 68 (43 mg, 0.15 mmol) in isopropanol (380 µL) and water (115 µL was added chloro (cyclopentadienyl) [bis(diphenylphosphino) methane]ruthenium (29 mg, 5 mol %) and the reaction mixture was heated for 16 hours at 100° C. LC-MS analysis of the reaction indicated that the reaction was complete. The reaction mixture was diluted with ethyl acetate (2 mL), washed with saturated $NaHCO_3$ (2 mL), separated and dried over magnesium sulfate. Concentration afforded crude compound 72 as a colorless oil. HPLC-MS $t_R$=2.07 min ($UV_{254\ nm}$); mass calculated for formula $C_{18}H_{25}NO_3$ 303.2, observed LCMS m/z 248.2 (M+H−$^t$Bu).

Part B:

To a solution of compound 72 (0.15 mmol) in 1,2-dichloroethane (3 mL) and acetic acid (300 µL) was added morpholine (26 uL, 0.3 mmol) and sodium triacetoxyborohydride (38 mg, 0.18 mmol) and the reaction mixture was stirred at room temperature for 1 hour. LC-MS analysis of the reaction indicated that the reaction was complete. The volatiles were removed in vacuo, and the residue re-dissolved in ethyl acetate (2 mL), washed with saturated $NaHCO_3$ (2 mL), separated and dried over magnesium sulfate. Concentration afforded crude compound 74 as a colorless oil. HPLC-MS $t_R$=1.36 min ($UV_{254\ nm}$); mass calculated for formula $C_{22}H_{34}N_2O_3$ 374.3, observed LCMS m/z 375.3 (M+H).

Part C:

Compound 74 was prepared from compound 73 using the hydrolysis conditions described in Example 1, Part B. HPLC- MS $t_R$=0.27 min ($UV_{254\ nm}$), mass calculated for formula $C_{17}H_2N_2O$ 274.2, observed LCMS m/z 275.2 (M+H).

Example 9

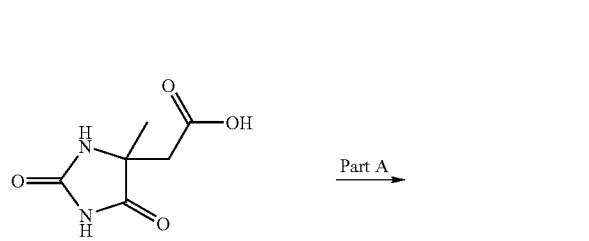

Part A:

To a solution of compound 3 (0.12 mmol) and HATU (68 mg, 0.18 mmol) in DMF (2 mL) was added amine building block (1.2 equivalents) and diisopropylethylamine (69 µL, 0.40 mmol). The reaction mixture was stirred at room temperature for 18 hours. LC-MS analysis of the reaction indicated that the reaction was complete. The volatiles were removed in vacuo, ethyl acetate was added, and the organic solution washed successively with saturated $NaHCO_3$ (×1), water (×1), brine (×1)$_5$ dried over magnesium sulfate and concentrated. Purification by preparative LC afforded compounds 75-77 (80-90% yield).

The following compounds were synthesized using this procedure:

Example 10

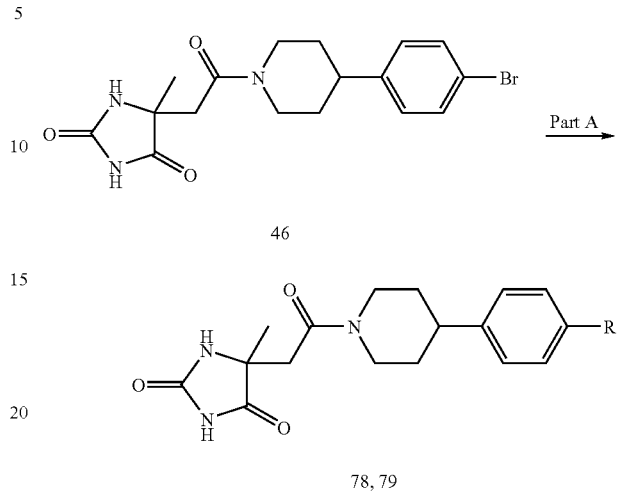

Part A:

To a solution of compound 46 (0.013 mmol) in dioxane (2 mL) was added boronic acid building block (2 equivalents), potassium phosphate (0.04 mmol) and dichloro[11'-bis(diphenylphosphino)ferrocene]palladium (II) dichloromethane (20 mol %). The reaction mixture was de-gassed, flushed with argon and heated at 90° C. for 16 hours. LC-MS analysis of the reaction indicated that the reaction was complete. The precipitates were removed by passing through a plug of celite, washed through with ethyl acetate and the filtrate concentrated. Purification by Preparative LC afforded compounds 78 and 79.

The following compounds were synthesized using this procedure:

| Serial # | Structure | Exact mass | MS m/z ($M^+ + H$) | Ret. Time (min) |
|---|---|---|---|---|
| 75 | ![structure] | 339.1 | 340.1 | 3.51 |
| 76 | ![structure] | 343.2 | 344.2 | 4.11 |
| 77 | ![structure] | 428.2 | 429.2 | 1.98 |

| Serial # | Structure | Exact mass | MS m/z (M+ + H) | Ret. Time (min) |
|---|---|---|---|---|
| 78 | 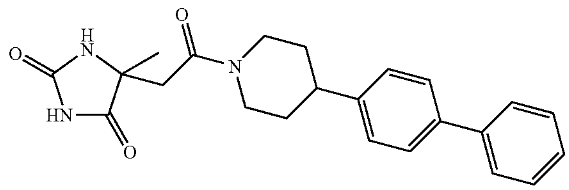 | 391.2 | 392.2 | 4.46 |
| 79 | 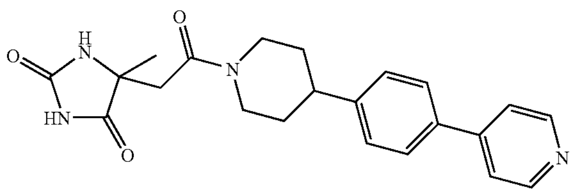 | 392.2 | 393.2 | 1.94 |

Example 11

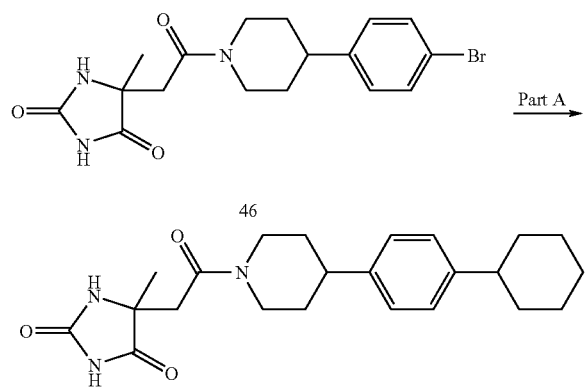

Part A:

To a solution of compound 46 (0.013 mmol) in dioxane (2 mL) is added cyclohexylboronic acid (2 equivalents), potassium phosphate (0.04 mmol) and dichloro[1,1'-bis(diphenylphosphino)ferrocene]palladium (1) dichloromethane (20 mol %). The reaction mixture is de-gassed, flushed with argon and heated at 90° C. for 16 hours. The precipitates are removed by passing through a plug of celite, washed through with ethyl acetate and the filtrate concentrated. Purification by preparative LC affords compound 80.

The following compound is synthesized using this procedure:

| Serial # | Structure | Exact mass | MS m/z (M+ + H) | Ret. Time (min) |
|---|---|---|---|---|
| 80 | 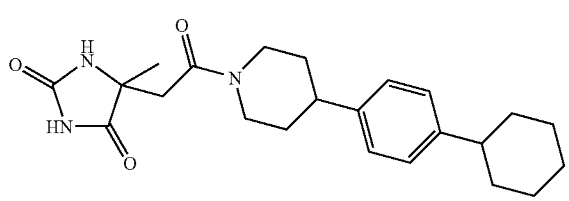 | 397.2 | | |

Example 12

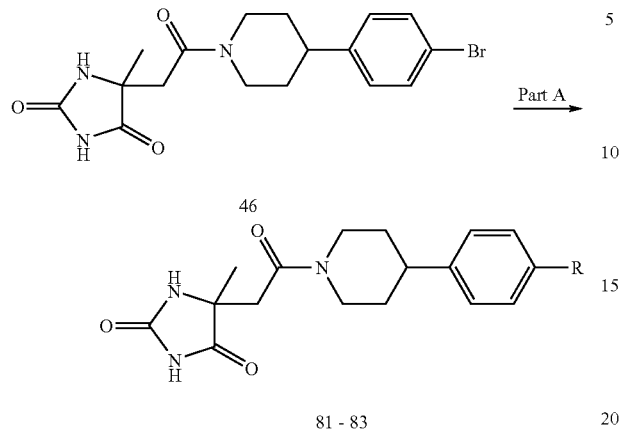

Part A:
To a solution of compound 46 (0.025 mmol) in toluene (1 mL) is added amine building block (1.3 equivalents), potassium carbonate (0.053 mmol), copper iodide (10 mol %) and trans-(1R,2R)—N,N'-bismethyl-1,2-cyclohexane diamine (40 mol %). The reaction mixture is flushed with argon and heated at 110° C. for 16 hours. The precipitates are removing by passing through a plug of celite, washed through with ethyl acetate and the filtrate concentrated. Purification by preparative LC affords compounds 81-83.

The following compounds were synthesized using this procedure:

Example 13

Example 12

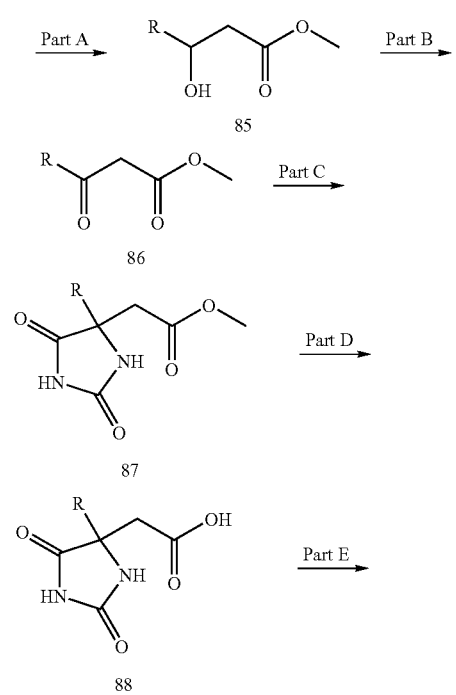

| Serial # | Structure | Exact mass | MS m/z (M+ + H) | Ret. Time (min) |
|---|---|---|---|---|
| 81 | 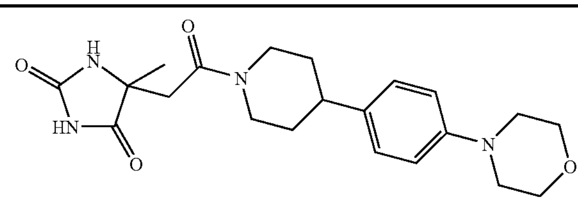 | | 400.2 | |
| 82 | 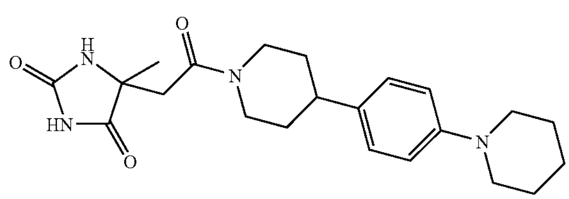 | | 398.2 | |
| 83 | 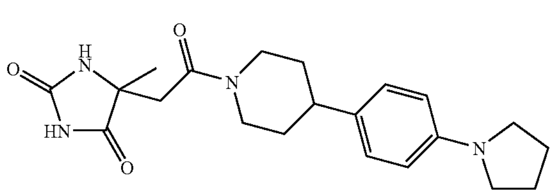 | | 384.2 | |

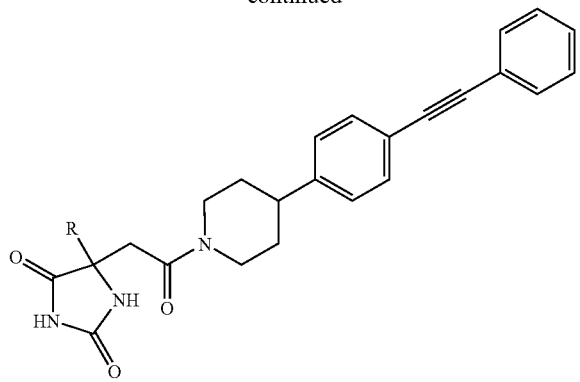

89 - 103

Part A:

To a solution of aldehyde (0.44 mmol) in THF (2 mL) is added Wilkinson's catalyst (5 mot %) and methyl bromoacetate (1 equivalent). The reaction mixture is cooled to 0° C., diethyl zinc (2.2 equivalents) is added and the reaction mixture stirred for an additional 5 minutes at 0° C. The reaction is quenched by the addition of saturated $NaHCO_3$, extracted with ethyl acetate, dried and purified by flash chromatography to afford compound 85.

Part B:

To a solution of compound 84 (2.86 mmol) in DCM (20 mL) is added Dess-Martin periodinane (1.1 equivalent) and the reaction mixture stirred at room temperature for 16 hours. The reaction is quenched by the addition of sodium thiosulfate (7 equivalents) in saturated $NaHCO_3$, stirred for an additional 10 minutes, extracted with DCM, dried and purified by flash chromatography to afford compound 86.

Part C:

Compound 87 is prepared from compound 86 using the hydantoin forming reaction described in Example 1, Part A.

Part D:

Compound 88 is prepared from compound 87 using the hydrolysis conditions described in Example 2, Part B.

Part E:

Compounds 89-103 are prepared using the peptide forming reactions described in Example 4, Part A.

BOC- and t-butyl ether protecting groups are hydrolyzed using conditions described in Example 3C, Part B.

The following compounds are synthesized using this procedure:

| Serial # | Structure | Exact mass | MS m/z ($M^+ + H$) | Ret. Time (min) |
|---|---|---|---|---|
| 89 | 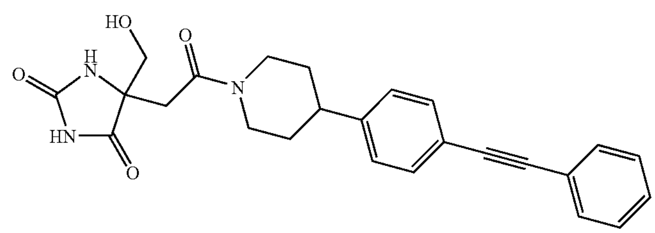 | | 400.2 | |
| 90 | 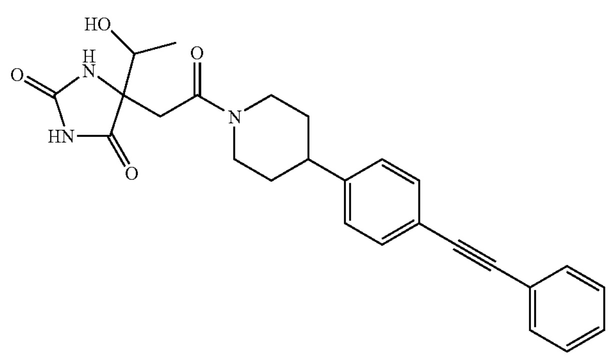 | | 445.2 | |
| 91 | 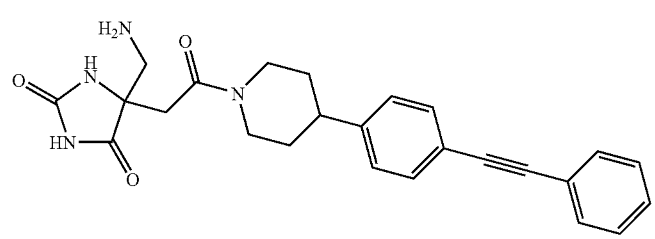 | | 430.2 | |

| Serial # | Structure | Exact mass | MS m/z (M⁺ + H) | Ret. Time (min) |
|---|---|---|---|---|
| 92 | 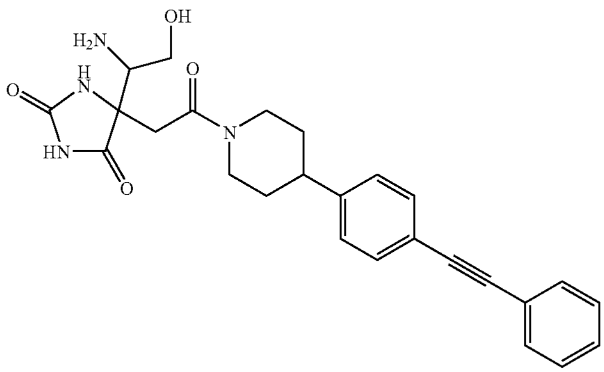 | | 460.2 | |
| 93 | 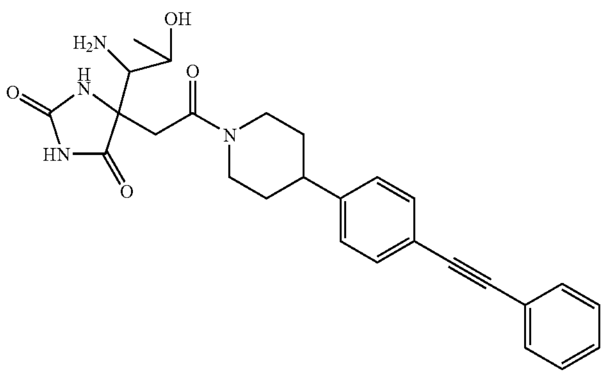 | | 474.2 | |
| 94 | 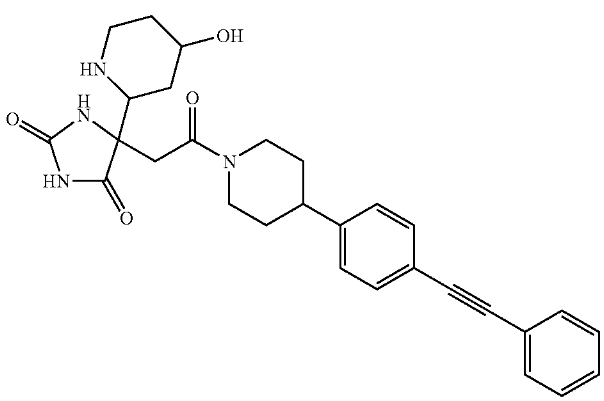 | | 500.2 | |
| 95 | 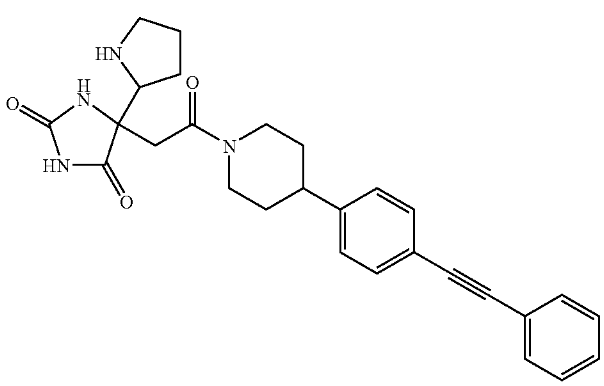 | | 470.2 | |

| Serial # | Structure | Exact mass | MS m/z (M+ + H) | Ret. Time (min) |
|---|---|---|---|---|
| 96 | 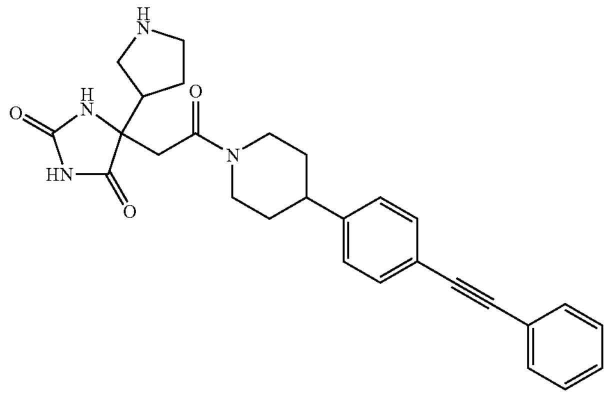 | | 470.2 | |
| 97 | 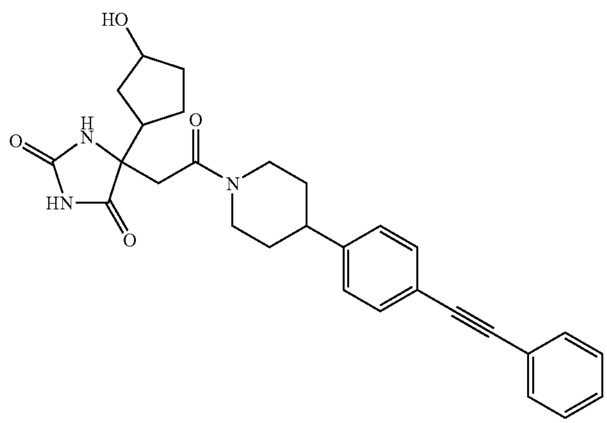 | | 485.2 | |
| 98 | 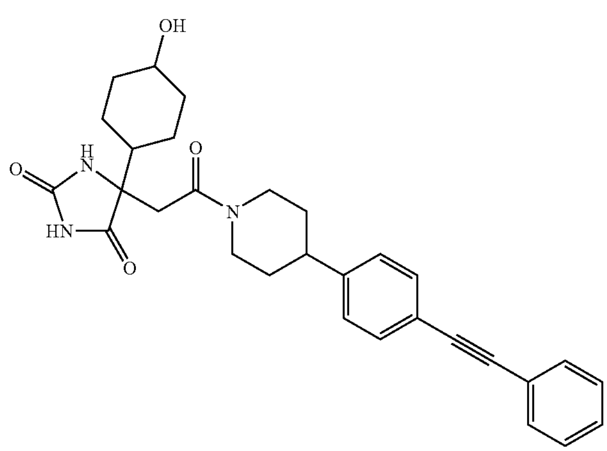 | | 499.3 | |

-continued

| Serial # | Structure | Exact mass | MS m/z (M⁺ + H) | Ret. Time (min) |
|---|---|---|---|---|
| 99 | 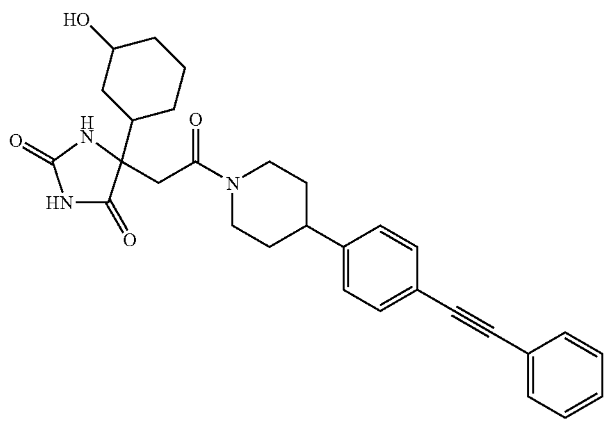 | | 499.3 | |
| 100 | 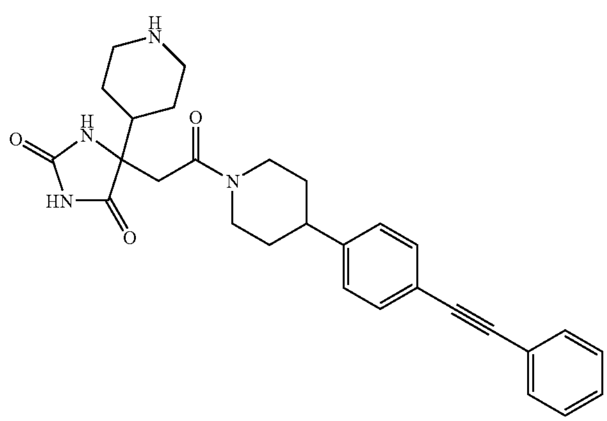 | | 484.3 | |
| 101 | 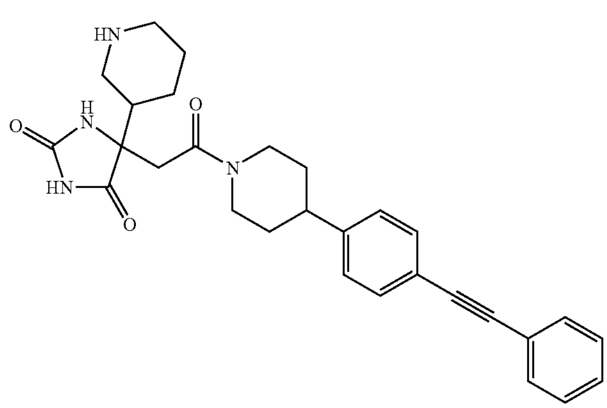 | | 484.3 | |

-continued

| Serial # | Structure | Exact mass | MS m/z (M+ + H) | Ret. Time (min) |
|---|---|---|---|---|
| 102 | 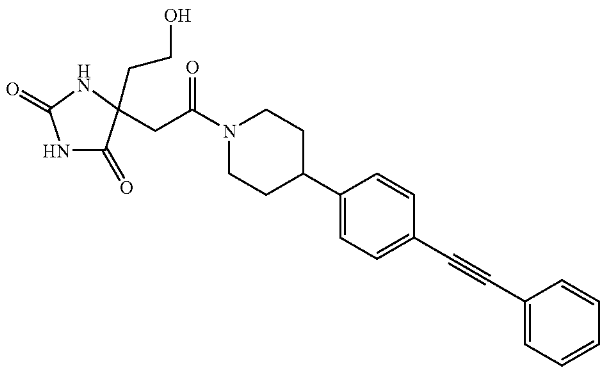 | | 445.2 | |
| 103 | 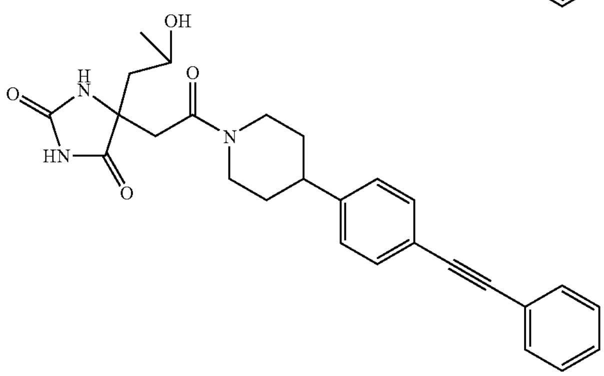 | | 459.2 | |

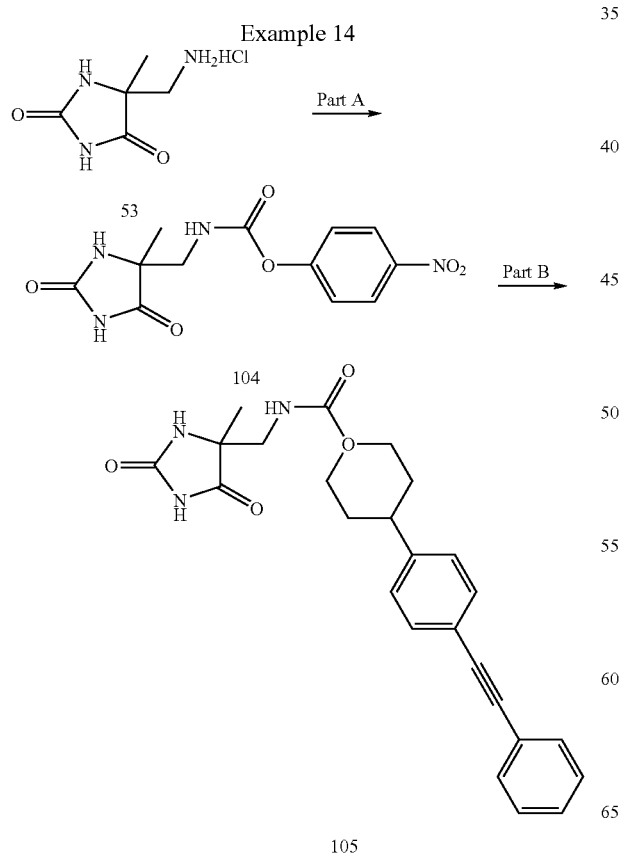

Example 14

Part A:

A solution of compound 53 (0.37 mmol) in THF (3 mL) is added over 15 minutes to a stirring solution of 4-nitrophenyl-chloroformate (1.2 equivalents) and DIEA (3 equivalents) in THF (3 mL) at 0° C. The reaction mixture is warmed to room temperature and stirred for an additional 16 hours. Ethyl acetate is added, and the reaction mixture washed with 1N HCl and brine dried over magnesium sulfate and concentrated. Purification by flash chromatography affords compound 104.

Part B;

To a solution of compound 104 (0.2 mmol) in DCM (2 mL) is added compound 22 (1.2 equivalents) and DIEA (3 equivalents). The reaction mixture is heated at 55° C. for 2 hours. Concentration and purification by preparative LC affords compound 105.

The following compound is synthesized using this procedure:

| Serial # | Structure | Exact mass | MS m/z (M+ + H) | Ret. Time (min) |
|---|---|---|---|---|
| 105 | 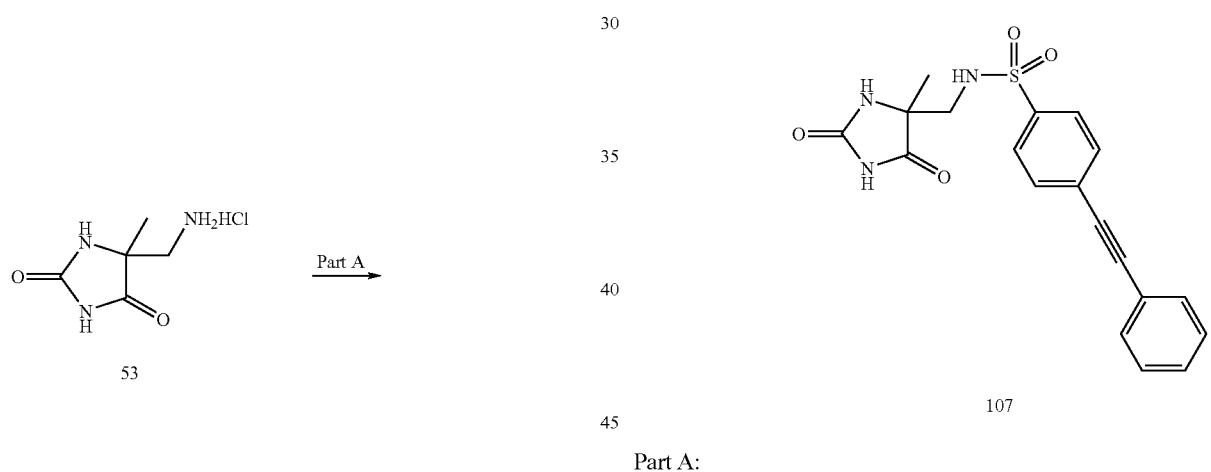 | | 403.2 | |

Example 15

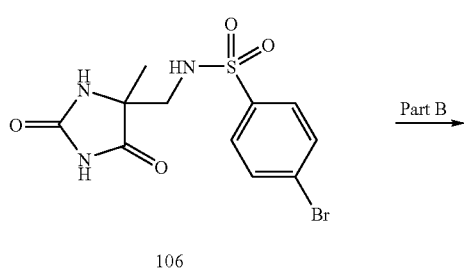

Part A:

A solution of compound 53 (0.2 mmol) and DIEA (3 equivalents) in DCM (1 mL) is added over 15 minutes to a stirring solution of 4-bromophenylsulfonyl chloride (1.2 equivalents) in DCM (2 mL) at 0° C. The reaction mixture is warmed to room temperature and stirred for an additional 16 hours. DCM is added, and the reaction mixture washed with 1N HCl and brine, dried over magnesium sulfate and concentrated. Purification by flash chromatography affords compound 104.

Part B:

Compound 107 is prepared from compound 106 using the Sonogashira coupling reaction described in Example 3C, Part B.

The following compound is synthesized using this procedure:

| Serial # | Structure | Exact mass | MS m/z (M+ + H) | Ret. Time (min) |
|---|---|---|---|---|
| 107 | 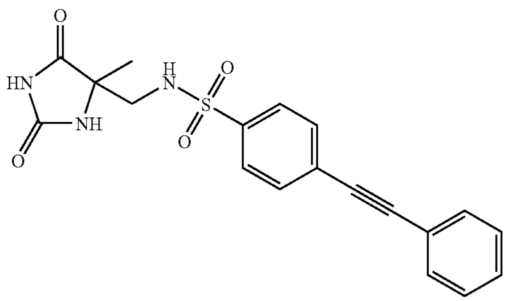 | | 383.1 | |

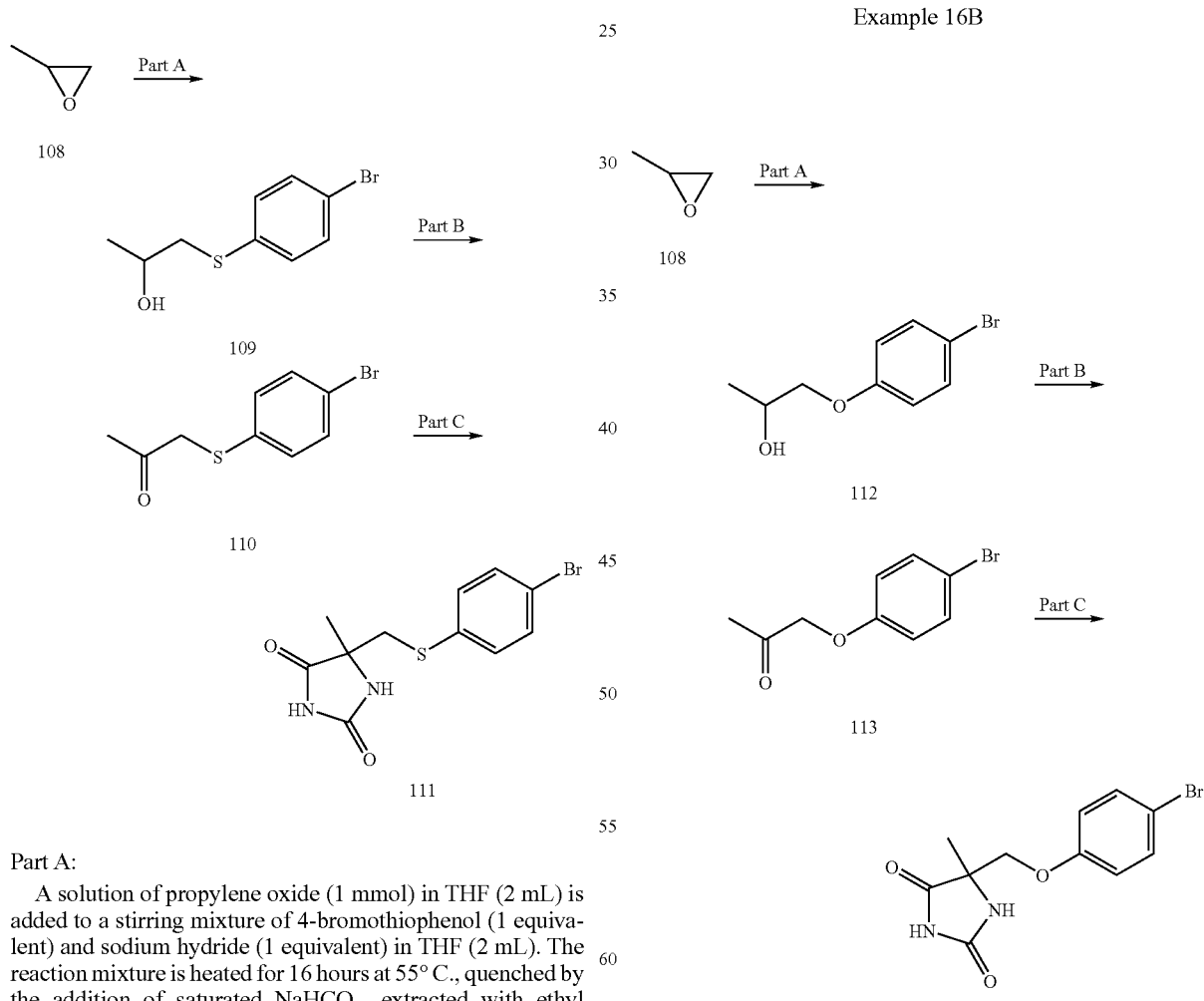

Example 16

Example 16A

Part A:

A solution of propylene oxide (1 mmol) in THF (2 mL) is added to a stirring mixture of 4-bromothiophenol (1 equivalent) and sodium hydride (1 equivalent) in THF (2 mL). The reaction mixture is heated for 16 hours at 55° C., quenched by the addition of saturated NaHCO$_3$, extracted with ethyl acetate, dried and purified by flash chromatography to afford compound 109.

Part B:

Compound 110 is prepared from compound 109 using the oxidation conditions described in Example 13, Part B.

Part C:

Compound 111 is prepared from compound 110 using the hydantoin forming reaction described in Example 1, Part A.

Example 16B

Compound 114 is prepared from propylene oxide (108) and 4-bromophenol using the conditions described in Example 16A: Part A-Part C.

Example 16C

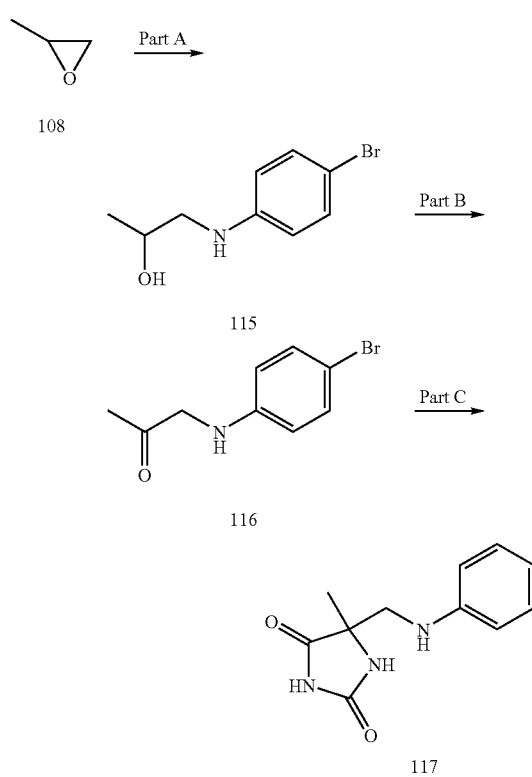

Compound 117 is prepared from propylene oxide (108) and 4-bromoaniline using the conditions described in Example 16A, Part A-Part C.

Example 17

Example 17A

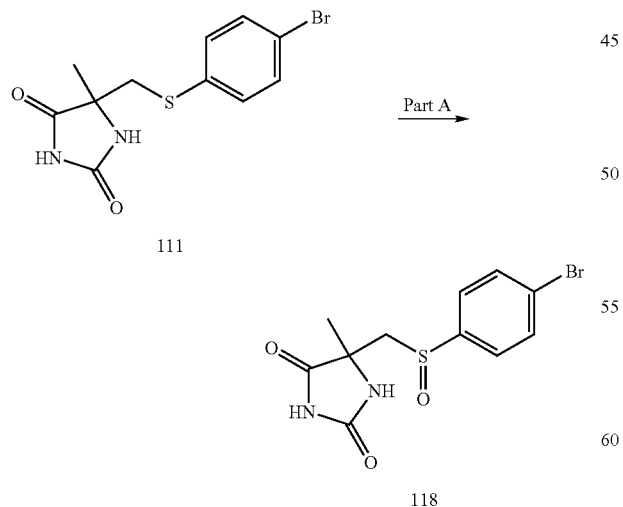

Part A:

3-Chloroperoxybenzoic acid (1 equivalent) is added to a stirring solution of compound 111 (1 mmol) in DCM (2 mL). The reaction mixture is stirred for 16 hours at room temperature, quenched by the addition of saturated NaHCO$_3$, extracted with ethyl acetate, dried and purified by flash chromatography to afford compound 118.

Example 17B

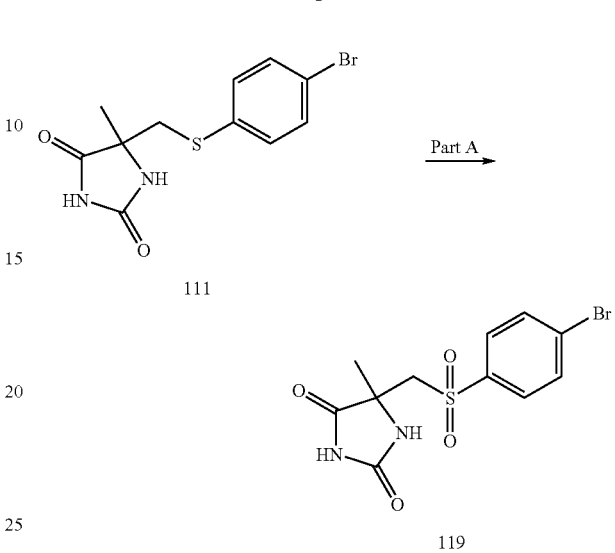

Part A:

3-Chloroperoxybenzoic acid (2.2 equivalents) is added to a stirring solution of compound 111 (1 mmol) in DCM (2 mL). The reaction mixture is stirred for 16 hours at room temperature, quenched by the addition of saturated NaHCO$_3$, extracted with ethyl acetate, dried and purified by flash chromatography to afford compound 119.

Example 18

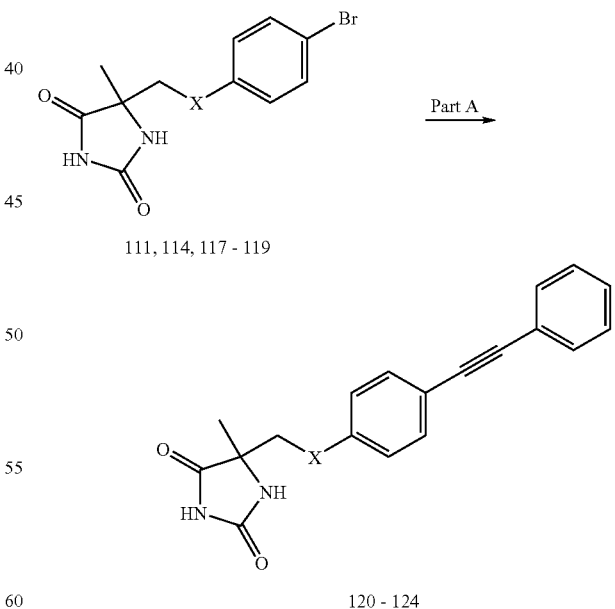

Part A:

Compounds 120-124 are prepared from compounds 111, 114 and 117-119 respectively using the Sonogashira coupling reaction described in Example 3C, Part B.

The following compounds are synthesized using this procedure:

| Serial # | Structure | Exact mass | MS m/z (M⁺ + H) | Ret. Time (min) |
|---|---|---|---|---|
| 120 | 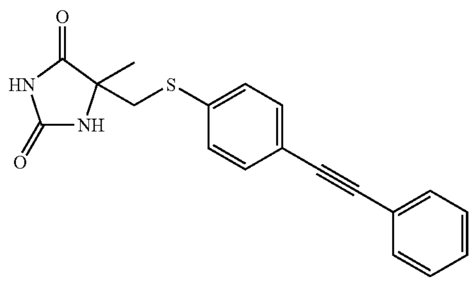 | | 336.1 | |
| 121 | 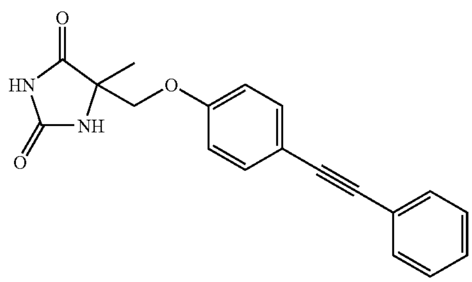 | | 320.1 | |
| 122 | 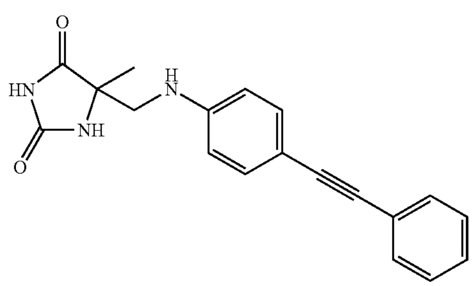 | | 319.1 | |
| 123 | 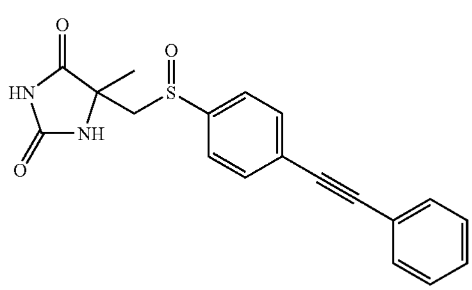 | | 352.1 | |
| 124 | 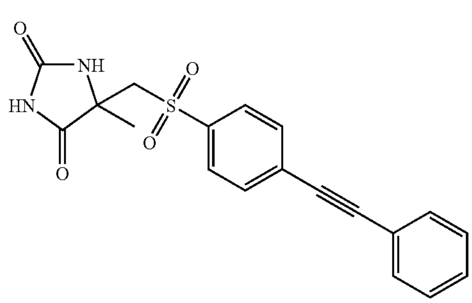 | | 368.1 | |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each and every document referred to in this patent application is incorporated herein by reference in its entirety for all purposes.

What is claimed is:

1. A compound selected from the group consisting of:

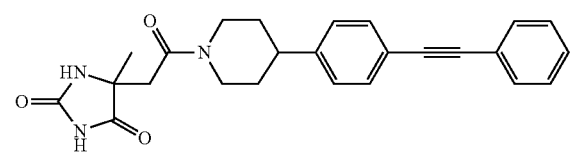

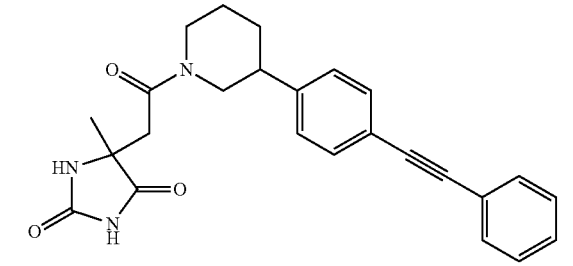

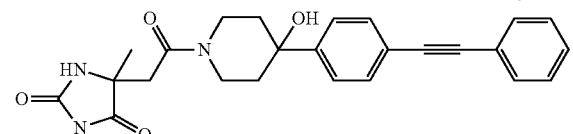

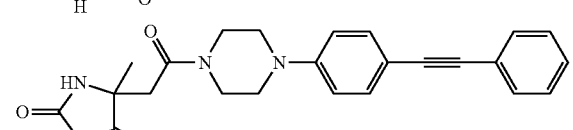

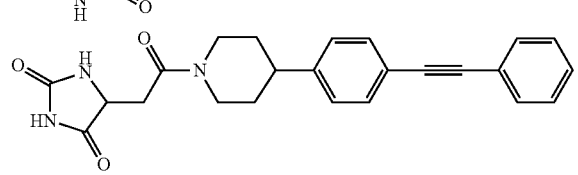

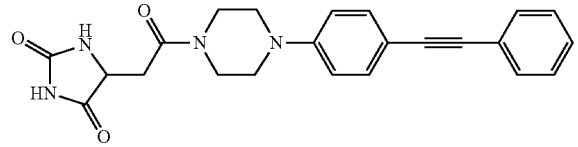

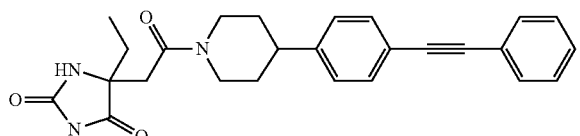

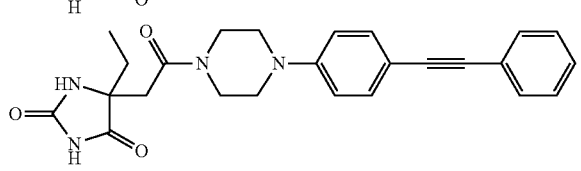

-continued

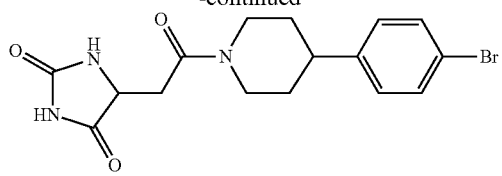

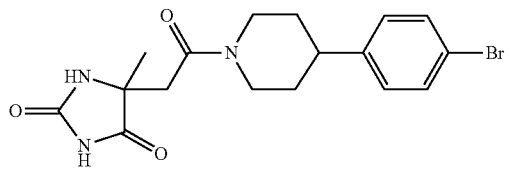

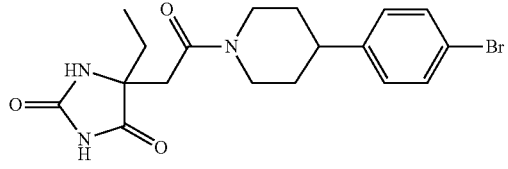

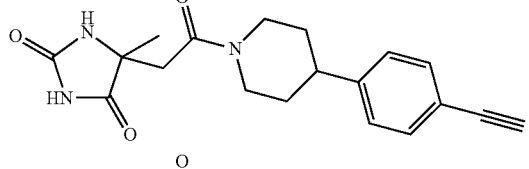

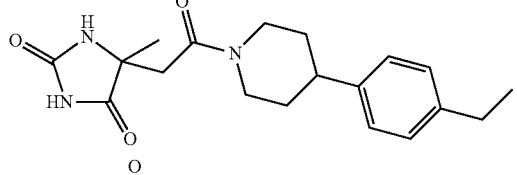

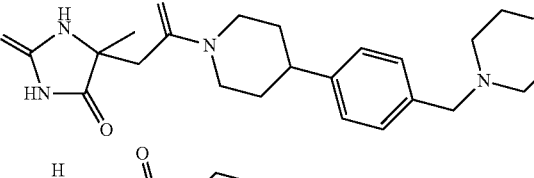

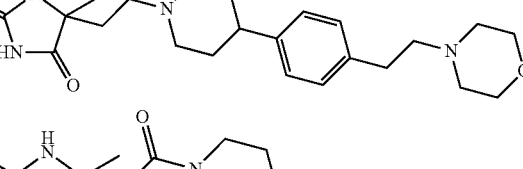

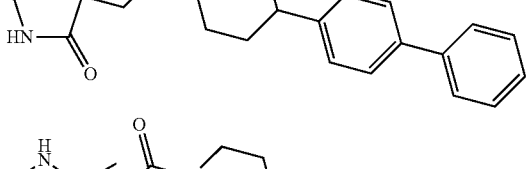

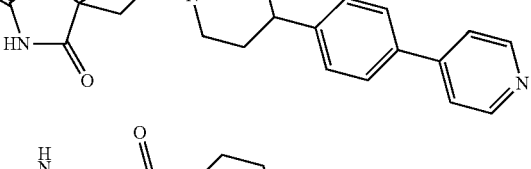

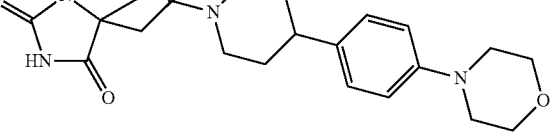

85
-continued
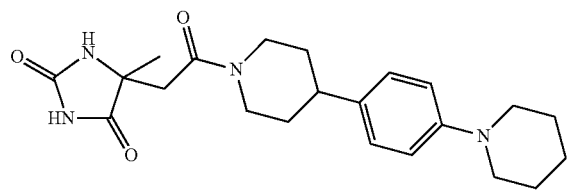
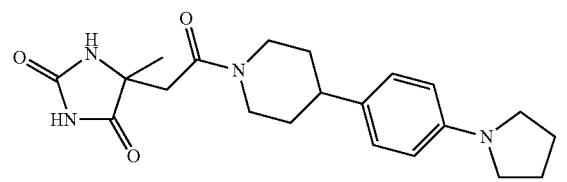
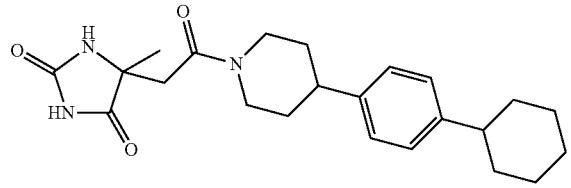
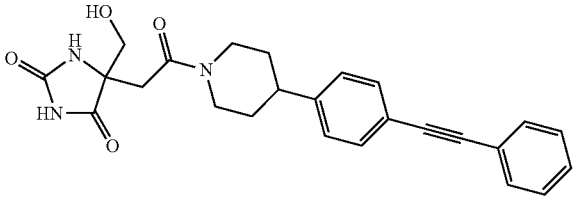
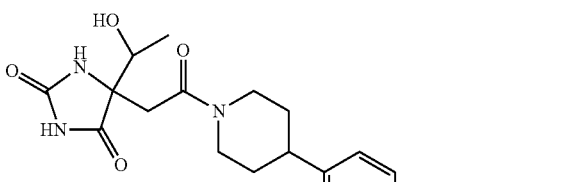
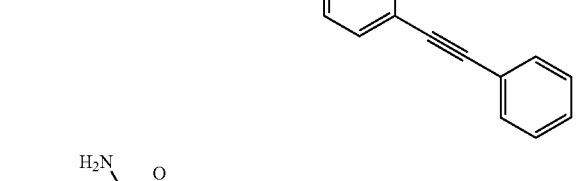
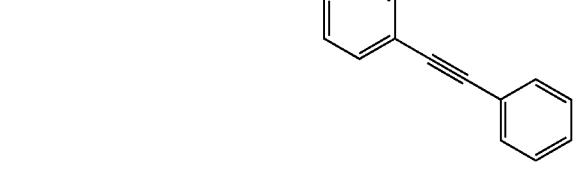
86
-continued
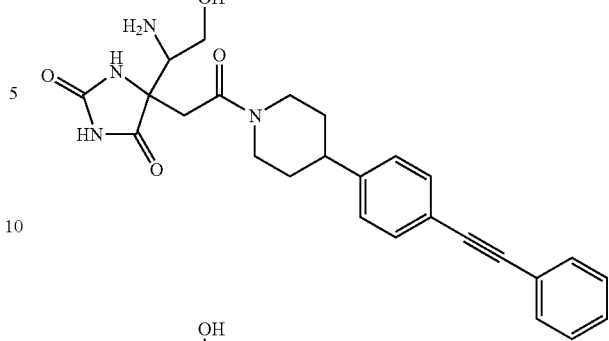
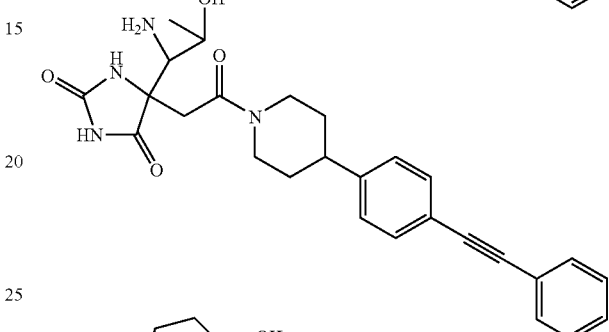
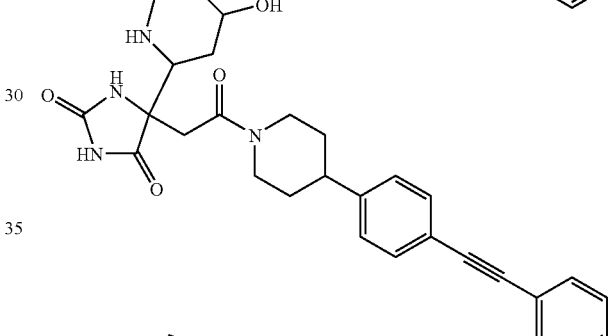
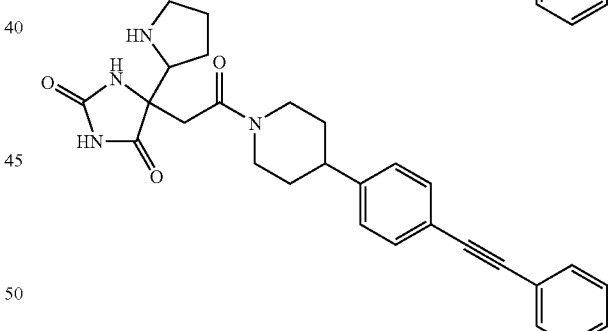
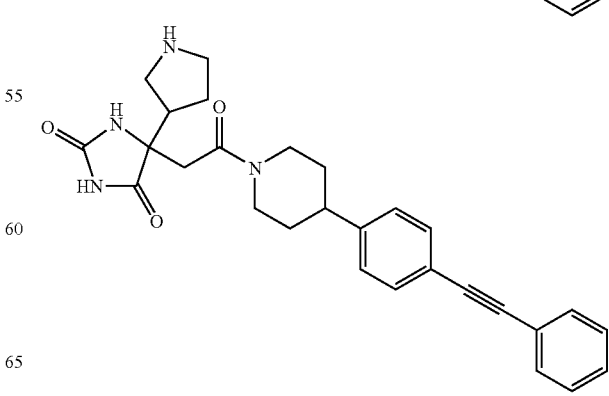

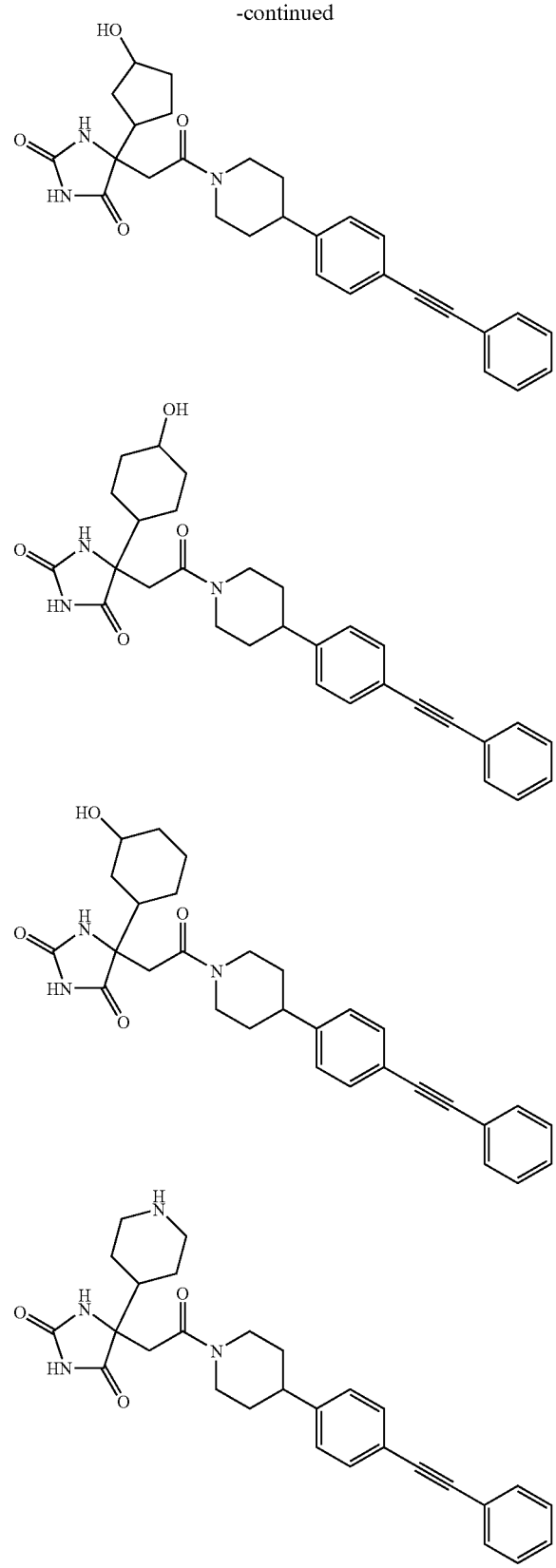
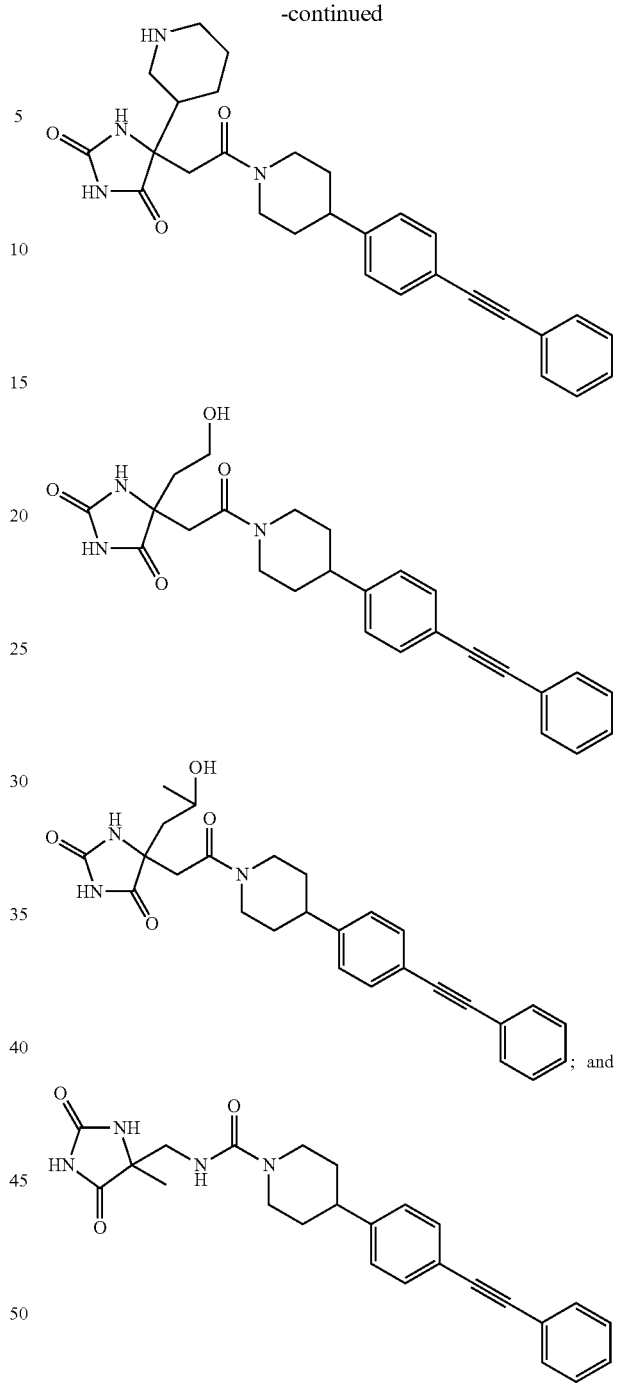
or a pharmaceutically acceptable salt or ester thereof.
2. A pharmaceutical composition comprising at least one compound of claim 1, or a pharmaceutically acceptable salt, or ester thereof, in combination with at least one pharmaceutically acceptable carrier.
3. The compound of claim 1, or a pharmaceutically acceptable salt thereof.
* * * * *